(12) United States Patent
Zhang et al.

(10) Patent No.: US 9,884,049 B2
(45) Date of Patent: Feb. 6, 2018

(54) MICROBICIDAL COMPOSITION COMPRISING AN OCTOXYNOL AND A QUINOLIZIDINE ALKALOID COMPOUND OR A SOURCE THEREOF

(71) Applicant: NOVICOL INTERNATIONAL HOLDING INC., Ottawa (CA)

(72) Inventors: Xuewu Zhang, Lueyang (CN); Eric Leire, Summerfield, NC (US)

(73) Assignee: ORION BIOTECHNOLOGY CANADA LTD., Ottawa (CA)

( * ) Notice: Subject to any disclaimer, the term of this patent is extended or adjusted under 35 U.S.C. 154(b) by 135 days.

(21) Appl. No.: 14/796,618

(22) Filed: Jul. 10, 2015

(65) Prior Publication Data

US 2016/0015696 A1    Jan. 21, 2016

Related U.S. Application Data

(60) Provisional application No. 62/056,764, filed on Sep. 29, 2014, provisional application No. 62/028,986, filed on Jul. 25, 2014, provisional application No. 62/024,092, filed on Jul. 14, 2014.

(51) Int. Cl.

| | | |
|---|---|---|
| A61K 31/48 | (2006.01) | |
| A61K 31/4375 | (2006.01) | |
| A61K 31/08 | (2006.01) | |
| A61K 36/489 | (2006.01) | |
| A61K 9/06 | (2006.01) | |
| A61K 9/00 | (2006.01) | |
| A61K 36/886 | (2006.01) | |

(52) U.S. Cl.
CPC ........ *A61K 31/4375* (2013.01); *A61K 9/0031* (2013.01); *A61K 9/0034* (2013.01); *A61K 9/06* (2013.01); *A61K 31/08* (2013.01); *A61K 36/489* (2013.01); *A61K 36/886* (2013.01)

(58) Field of Classification Search
None
See application file for complete search history.

(56) References Cited

U.S. PATENT DOCUMENTS

| 4,707,362 | A | 11/1987 | Nuwayser |
|---|---|---|---|
| 4,844,901 | A | 7/1989 | Keplinger et al. |
| 4,999,342 | A | 3/1991 | Ahmad et al. |
| 5,518,730 | A | 5/1996 | Fruiz |
| 6,706,276 | B2 | 3/2004 | Garg et al. |
| 6,770,306 | B1 | 8/2004 | Zeng |
| 7,262,170 | B2 | 8/2007 | Zeng |
| 7,285,517 | B2 | 10/2007 | Ahmad et al. |
| 7,384,657 | B2 | 6/2008 | Young |
| 8,153,166 | B2 | 4/2012 | Lin |
| 8,198,293 | B2 | 6/2012 | Chia |
| 8,309,143 | B2 | 11/2012 | Campbell et al. |
| 8,518,434 | B2 | 8/2013 | Livingston et al. |
| 8,557,251 | B2 | 10/2013 | Garcon et al. |
| 8,703,171 | B2 * | 4/2014 | Schaub ................ A61K 9/0034  424/430 |
| 2002/0151521 | A1 | 10/2002 | Burke et al. |
| 2003/0003095 | A1 | 1/2003 | Sunberg et al. |
| 2003/0207776 | A1 | 11/2003 | Shefer et al. |
| 2004/0022808 | A1 | 2/2004 | Colau et al. |
| 2006/0062866 | A1 | 3/2006 | Neurath et al. |
| 2008/0166383 | A1 | 7/2008 | Zhou et al. |
| 2008/0193489 | A1 | 8/2008 | De Armond et al. |
| 2009/0004294 | A1 * | 1/2009 | Margulies ............ A61K 9/0034  424/649 |
| 2009/0142313 | A1 | 6/2009 | Telling et al. |
| 2009/0169653 | A1 | 7/2009 | Lin |
| 2010/0151029 | A1 | 6/2010 | Gruening et al. |
| 2010/0152691 | A1 | 6/2010 | Seidling et al. |
| 2010/0252050 | A1 | 10/2010 | Grogan et al. |
| 2010/0285097 | A1 | 11/2010 | Talling et al. |
| 2011/0020350 | A1 | 1/2011 | Klinefelter |

(Continued)

FOREIGN PATENT DOCUMENTS

| CN | 1348746 A | 5/2002 |
|---|---|---|
| CN | 1402981 A | 3/2003 |

(Continued)

OTHER PUBLICATIONS

Johnson, W. Jr. Int. J. Toxicology, 2004; 23 Suppl 1:59-111 (Abstract only).*
Cao et al., A combination of a microemulsion and a phospholipid complex for topical delivery of oxymatrine. *Arch. Pharma. Res.* 34(4): 551-562 (2011).
Hughes et al., The search for a topical dual action spermicide/microbicide. *Curr. Med. Chem.* 14(7): 775-96 (2007). Abstract Only.
Kim et al., Medicinal herbal extracts of *Sophorae radix*, *Acanthopanacis cortex*, *Sanguisorbae radix* and *Torilis fructus* inhibit coronavirus replication in vitro. *Antiviral Ther.* 15: 697-709 (2010).

(Continued)

*Primary Examiner* — Sreeni Padmanabhan
*Assistant Examiner* — Jeanmarie Calvillo
(74) *Attorney, Agent, or Firm* — Marshall, Gerstein & Borun LLP

(57) ABSTRACT

The present invention provides microbicidal compositions comprising an octoxynol and a quinolizidine alkaloid compound or a source thereof, and methods of using the compositions. The quinolizidine alkaloid compound has a structure:

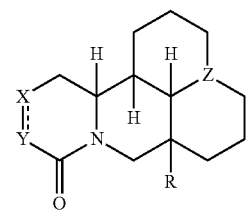

or a pharmaceutically acceptable salt, solvate or stereoisomer thereof.

9 Claims, 17 Drawing Sheets

(56) References Cited

U.S. PATENT DOCUMENTS

| | | |
|---|---|---|
| 2011/0144143 A1 | 6/2011 | Sun et al. |
| 2011/0189257 A1 | 8/2011 | Chin et al. |
| 2011/0206747 A1 | 8/2011 | Lagny et al. |
| 2012/0046556 A1 | 2/2012 | Block |

FOREIGN PATENT DOCUMENTS

| | | | |
|---|---|---|---|
| CN | 1410060 A | 4/2003 | |
| CN | 1159011 C | * 7/2004 | ......... A61K 31/4375 |
| CN | 1517116 A | 8/2004 | |
| CN | 1751723 A | 3/2006 | |
| CN | 1872026 A | 12/2006 | |
| CN | 100418528 C | 9/2008 | |
| CN | 100418578 C | 12/2008 | |
| CN | 100592912 C | 3/2010 | |
| CN | 101757140 B | 9/2010 | |
| CN | 101912376 A | 12/2010 | |
| CN | 101991605 A | 3/2011 | |
| CN | 102091049 A | 6/2011 | |
| CN | 102246827 A | 11/2011 | |
| CN | 103520107 A | 1/2014 | |
| CN | 104510767 A | 4/2015 | |
| EP | 2062568 A1 | 5/2009 | |
| WO | WO-2000/72839 A1 | 12/2000 | |
| WO | WO-2007/074478 A1 | 7/2007 | |
| WO | WO-2011/112166 A1 | 9/2011 | |
| WO | WO-2014/113784 A1 | 7/2014 | |
| WO | WO-2014/149160 A1 | 9/2014 | |

OTHER PUBLICATIONS

Meng et al., Spermicidal effect of alcohol extracts from different ratios of Sophora flavescens Ait/Chinese Bulbul in vitro. *Natl. J. Androl.* 18.1, 83:7 (Jan. 2012). Abstract Only.

Zhao et al., Preparation and skin penetration of matrine loaded microemulsion. *Pharm. Care Res.* 8(4): 252-4 (2008). Abstract Only.

International Search Report and Written Opinion issued in connection with International Application No. PCT/CA2015/050642, dated Sep. 2, 2015, pp. 1-11.

* cited by examiner

Phosphate saline

Negative Control

Formulation A (2ml)

Formulation B (2ml)

Formulation C (2ml)

MICROBICIDAL COMPOSITION COMPRISING AN OCTOXYNOL AND A QUINOLIZIDINE ALKALOID COMPOUND OR A SOURCE THEREOF

CROSS REFERENCE TO RELATED APPLICATIONS

This application claims the benefit of U.S. Provisional Application No. 62/024,092, filed Jul. 14, 2014, entitled "MICROBICIDAL COMPOSITION COMPRISING AN OCTOXYNOL AND A *SOPHORA* EXTRACT", to Zhang et al.; U.S. Provisional Application No. 62/028,986, filed Jul. 25, 2014, entitled "MICROBICIDAL COMPOSITION COMPRISING AN OCTOXYNOL AND MATRINE AND/OR OXYMATRINE, OR A SOURCE THEREOF", to Zhang et al.; and U.S. Provisional Application No. 62/056,764, filed Sep. 29, 2014, entitled "MICROBICIDAL COMPOSITION COMPRISING AN OCTOXYNOL AND MATRINE AND/OR OXYMATRINE, OR A SOURCE THEREOF", to Zhang et al., incorporated herein by reference in their entirety.

FIELD

The present application relates to microbicidal compositions comprising an octoxynol and a quinolizidine alkaloid compound or a source thereof, and methods of using the compositions.

BACKGROUND

The increasing prevalence of sexually transmitted diseases (STDs) is a serious public health problem affecting physical contact, sexual activity, and relationships between individuals.

Examples of STDs include those caused by viral infection such as human immunodeficiency virus (HIV)/acquired immunodeficiency syndrome (AIDS), herpes simplex types 1 and 2, human papillomavirus (HPV), and hepatitis B; those caused by bacterial infection such as gonorrhea, syphilis, chancroid, and *chlamydia*; and those caused by infection of other microorganisms such as trichomoniasis and candidiasis. Of particular concern is HIV/AIDS, a fatal disease which presently infects millions of people worldwide and is considered pandemic by the World Health Organization (WHO).

Sexually active females who are susceptible to STD transmissions at the same time run high risks of unwanted pregnancy.

Surfactants have been used as active ingredients in contraceptive compositions. It is also known that some surfactants, such as nonoxynol-9 and octoxynol-9, demonstrated inhibitory activity on HIV infection. For example, WO00/72839 describes a spermicidally and virucidally effective formulation for vaginal application that comprises benzalkonium chloride and octoxynol-9.

However, frequent use of nonoxynol-9 as a vaginal contraceptive/microbicide has been associated with an increased risk of vaginal or cervical infection, irritation, or ulceration (Niruthisard et al., Sex Transm Dis. 18:176-79 (1991); Rekart, Defic Syndr. 5:425-27 (1992); Roddy et al., Int J STD & HIV. 4:165-70 (1993); Weir et al., Genitourin Med. 71:78-81 (1995)) which can enhance the susceptibility of the ectocervical epithelium and the endocervical mucosa to HIV-1 infection (Augenbraun et al. Infect Dis Clin North Am. 8:439-48 (1994); Weir et al., Genitourin Med. 71:78-81 (1995); Kreiss, JAMA. 268:477-82 (1992)).

From 1996 to 2000, a clinical trial sponsored by the United Nation (UN) followed nearly 1,000 sex workers in Africa who used nonoxynol-9 or a placebo. The HIV infection rate among those using nonoxynol-9 was about 50% higher than those who used the placebo.

Compositions and formulations comprising active ingredients that are not surfactants have also been developed for preventing the spread of STDs. CN 1517116 describes a composition comprising five herbal extracts from *Cnidium monnieri, Artemisia argyi, Sophoraflavescens, Isitidis tinctoria*, and *Brucea javanica*. US2006/0062866 describes a starch-pomegranate juice complex. WO2007/074478 describes condoms, gels, creams and vaginal pessaries comprising *Azadirachta indica* extract and/or *Carica papaya* extract. US2009/0004294 describes a lubricating composition comprising a colloidal metal. US2012/0046556 describes a composition comprising a dental irritant.

There remains a need for the development of compositions that are effective in preventing transmission of STDs and/or conception and, when used in body orifices and/or on genitalia, exhibit low systemic and/or local toxicity at the target mucosal membranes.

SUMMARY

In one aspect, there is provided a composition comprising (a) an octoxynol; and (b) a quinolizidine alkaloid compound or a source thereof, wherein the quinolizidine alkaloid compound, has a structure:

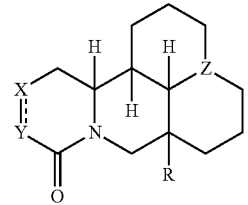

or a pharmaceutically acceptable salt, solvate or stereoisomer thereof, wherein:
R is H or OH;
X and Y are each $CH_2$ or CH; and
Z is N or NO.

In an embodiment of the composition as described herein, the quinolizidine alkaloid compound is matrine and/or oxymatrine.

In an embodiment of the composition as described herein, the source of the quinolizidine alkaloid compound is a *Sophora* extract.

In an embodiment, the composition as described herein comprises about 0.2% to about 3% of the quinolizidine alkaloid compound, or about 8% to about 30% of the source of the quinolizidine alkaloid compound, on a weight (g)/volume (mL) basis.

In an embodiment, the composition as described herein further comprises a moisturizing agent.

In an embodiment of the composition as described herein, the moisturizing agent is an *aloe* extract or allantoin.

In an embodiment of the composition as described herein, the octoxynol is octoxynol-9 or IGEPAL®CA-630.

In an embodiment, the composition as described herein further comprises a preservative.

In an embodiment, the composition as described herein further comprises one or more of an excipient, a buffering agent, and a lubricating agent.

In an embodiment, the composition as described herein is formulated as a gel.

In an embodiment, the composition as described herein comprises: about 0.05% to about 2.5% of octoxynol-9 or IGEPAL®CA-630 as the octoxynol on a volume/volume (mL) basis; about 0.2% to about 3% of matrine and/or oxymatrine as the quinolizidine alkaloid compound, or about 8% to about 30% of a source of matrine and/or oxymatrine, on a weight (g)/volume (mL) basis; and about 0.5% to about 5% of an *aloe* extract or allantoin as the moisturizing agent on a weight (g)/volume (mL) basis.

In an embodiment, the composition as described herein comprises: about 0.1% of octoxynol-9 or IGEPAL®CA-630 on a volume/volume (mL) basis; about 0.4% of matrine and/or oxymatrine, or about 20% of the source of matrine and/or oxymatrine, on a weight (g)/volume (mL) basis; and about 2% of the *aloe* extract or about 0.5% of allantoin on a weight (g)/volume (mL) basis.

In an embodiment, the composition as described herein comprises hydroxyethylcellulose (HEC).

In an embodiment, the composition as described herein has a pH between about 4.5 and about 5.6 and/or a viscosity between about 30 PaS and about 50 PaS.

In an embodiment, the composition as described herein is for use in prevention of conception and/or prevention of transmission of a sexually transmitted disease.

In another aspect, the present invention provides a method of prevention of conception and/or prevention of transmission of a sexually transmitted disease, said method comprising administering the composition of as described herein to a subject.

In an embodiment of the method as described herein, the subject is a human female, the composition as described herein is formulated as a gel, and the administration comprises discharging the composition into the vagina or anus of the human female.

In an embodiment of the method as described herein, the subject is a human male, the composition as described herein is formulated as a gel, and the administration comprises discharging the composition into the anus of the human male.

In another aspect, the present invention provides a kit for prevention of conception and/or prevention of transmission of a sexually transmitted disease, said kit comprising: a. the composition as described herein; b. an applicator; and c. optionally a prophylactic device.

In an embodiment of the kit as described herein, the prophylactic device is a condom.

Other aspects and features of the present invention will become apparent to those of ordinary skill in the art upon review of the following description of specific embodiments of the invention in conjunction with the accompanying figures.

BRIEF DESCRIPTION OF THE FIGURES

FIG. 2A shows VK2 cells, FIG. 2B shows End1 cells, and FIG. 2C shows Ect1 cells. The error bars represent standard deviations (±SD).

FIG. 3A shows phosphate saline, FIG. 3B shows the negative control, FIG. 3C shows Formulation A, FIG. 3D shows Formulation B, and FIG. 3E shows Formulation C.

DETAILED DESCRIPTION

Figure 1:
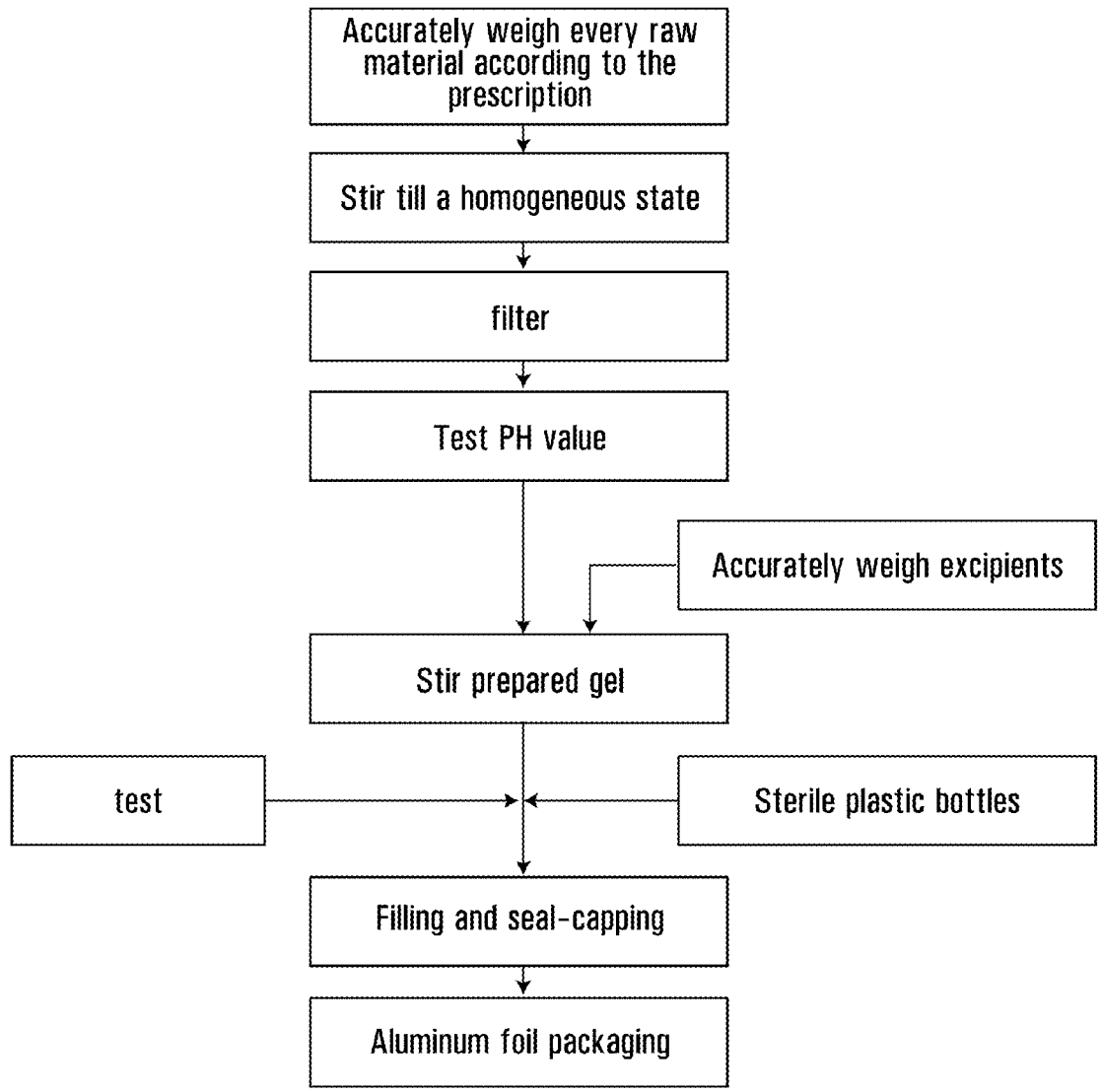
FIG. 1 shows an exemplary process of making a gel according to the invention.

Compositions, methods and kits of the present invention relate to prevention of conception and/or prevention of transmission of STDs. It has been found that a combination of (a) an octoxynol and (b) a quinolizidine alkaloid compound or a source thereof may be toxic to membranes of viruses and bacteria that cause STDs, but not to cells and normal flora at the target mucosal membranes. As used herein, "mucosal membrane" refers to a mucus-secreting membrane which lines all body cavities or passages that communicate with the exterior. For example, mucosal membranes include buccal, vaginal, or rectal membranes.

Furthermore, it has also been found that a quinolizidine alkaloid compound or a source thereof may enhance the microbicidal and/or spermicidal activities of an octoxynol, thereby making it possible to use a lower concentration of the octoxynol which may further improve the safety profile of compositions provided herein.

In some embodiments, the anti-viral activity (e.g., anti-HIV activity) of a composition of the present invention may be enhanced by at least about 10%, at least about 25%, at least about 50%, at least about 100%, at least about 200%, at least about 300%, or at least about 400%, compared to the octoxynol comprised therein. In some embodiments, the anti-viral activity (e.g., anti-HIV activity) of a composition of the present invention may be enhanced by up to about 100%, up to about 200%, up to about 300%, or up to about 400%, compared to the octoxynol comprised therein. In some embodiments, the anti-viral activity (e.g., anti-HIV activity) of a composition of the present invention may be enhanced by about 100% compared to the octoxynol comprised therein. In some embodiments, the anti-viral activity (e.g., anti-HIV activity) of a composition of the present invention may be enhanced by about 300% compared to the octoxynol comprised therein.

In some embodiments, the cytotoxicity of a composition of the present invention may be reduced by at least about 10%, at least about 15%, at least about 20%, at least about 25%, at least about 30%, at least about 40%, at least about 50%, at least about 60%, at least about 70%, at least about 75%, at least about 80%, at least about 90%, or at least about 95%, compared to the octoxynol comprised therein. In some embodiments, the cytotoxicity of a composition of the present invention may be reduced by up to about 15%, up to about 20%, up to about 25%, up to about 30%, up to about 40%, up to about 50%, up to about 60%, up to about 70%, up to about 75%, up to about 80%, up to about 90%, up to about 95%, or up to about 99%, compared to the octoxynol comprised therein. In some embodiments, the cytotoxicity of a composition of the present invention may be reduced by about 15% compared to the octoxynol comprised therein. In some embodiments, the cytotoxicity of a composition of the present invention may be reduced by about 25% compared to the octoxynol comprised therein. In some embodiments, the cytotoxicity of a composition of the present invention may be reduced by about 50% compared to the octoxynol comprised therein.

Without being limited by theory, it is believed that a quinolizidine alkaloid compound (such as matrine and/or oxymatrine), or a source thereof (such as a *Sophora* extract), may protect cells and normal flora at mucosal membranes from the toxicity of an octoxynol (for example, by inhibiting inflammation via inhibiting nuclear factor kappa-light-chain-enhancer of activated B cells (NF-κB) activation) without masking the microbicidal and/or spermicidal activities of the octoxynol. A quinolizidine alkaloid compound or a source thereof may also synergistically interact with an octoxynol such that the combination thereof has improved microbicidal and/or spermicidal activities than the octoxynol alone.

Compositions provided herein may prevent inflammatory cell infiltration, epithelial lesion, hyperemia or edema at mucosal membranes, as well as protect normal flora at mucosal membranes. Compositions provided herein may also exhibit enhanced microbicidal and/or spermicidal activities than the individual component comprised therein.

It is to be understood that any numerical value inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

As used herein, "transmission of a sexually transmitted disease" refers to spread or transmission from one individual to another through sexual intercourse or other sexual contact.

Compositions

An octoxynol is an ethoxylated alkylphenol. Suitable octoxynols may include, but are not limited to, octoxynol-1, octoxynol-3, octoxynol-5, octoxynol-6, octoxynol-7, octoxynol-8, octoxynol-9, octoxynol-10, octoxynol-11, octoxynol-12, octoxynol-13, octoxynol-16, octoxynol-20, octoxynol-25, octoxynol-30, octoxynol-33, octoxynol-40, octoxynol-70, octoxynol-9 carboxylic acid, octoxynol-20 carboxylic acid, potassium octoxynol-12 phosphate, sodium octoxynol-2 ethane sulfonate, sodium octoxynol-2 sulfate, sodium octoxynol-6 sulfate, sodium octoxynol-9 sulfate, IGEPAL®CA-630 or a mixture thereof.

In some embodiments, the octoxynol is octoxynol-9 (also known as Triton X-100) having the formula of:

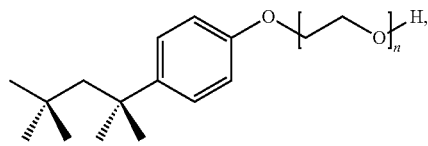

wherein n=9-10.

In some embodiments, the octoxynol is IGEPAL® CA-630 having the formula of:

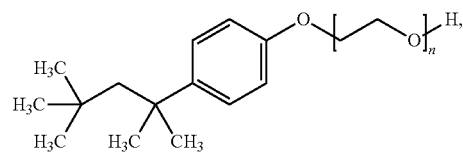

wherein n=8-10. IGEPAL® CA-630 can be purchased from Sigma-Aldrich® or Spectrum Chemical MFG Corp.

As used herein, a quinolizidine alkaloid compound has a structure:

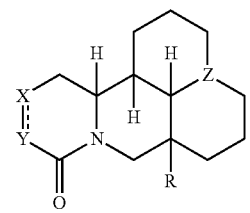

or a pharmaceutically acceptable salt, solvate or stereoisomer thereof, wherein:

R is H or OH;

X and Y are each $CH_2$ or CH; and

Z is N or NO. In some embodiments, R is H, X and Y are each $CH_2$, and Z is N. In some embodiments, R is H, X and Y are each $CH_2$, and Z is NO. In some embodiments, R is H, X and Y are each CH, and Z is N. In some embodiments, R is OH, X and Y are each CH$_2$, and Z is N.

As used herein, the term "pharmaceutically acceptable salt" includes acid addition or base salts. Suitable acid addition salts are formed from acids which form non-toxic salts. Examples may include, but are not limited to, the acetate, adipate, aspartate, benzoate, besylate, bicarbonate/carbonate, bisulfate/sulfate, borate, camphorsulfonate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts. Suitable base salts are formed from bases which form non-toxic salts. Examples may include, but are not limited to, the aluminium, arginine, benzathine, calcium, choline, diethylamine, diolamine, glycine, lysine, magnesium, meglumine, olamine, potassium, sodium, tromethamine, and zinc salts. For a review on suitable salts, see "Handbook of Pharmaceutical Salts: Properties, Selection, and Use" by Stahl and Wermuth (Wiley-VCH, 2011).

As used herein, the term "solvate" means a compound that further includes a stoichiometric or non-stoichiometric amount of solvent bound by non-covalent intermolecular forces. Where the solvent is water, the solvate is a hydrate.

As used herein, the term "stereoisomer" encompasses all stereomerically pure and stereomerically enriched compounds provided herein.

As used herein, the term "stereomerically pure" means a composition that comprises one stereoisomer of a compound and is substantially free of other stereoisomers of that compound. For example, a stereomerically pure composition of a compound having one chiral center will be substantially free of the opposite enantiomer of the compound. A stereomerically pure composition of a compound having two chiral centers will be substantially free of other diastereomers of the compound. A typical stereomerically pure compound comprises greater than about 80% by weight of one stereoisomer of the compound and less than about 20% by weight of other stereoisomers of the compound, greater than about 90% by weight of one stereoisomer of the compound and less than about 10% by weight of the other stereoisomers of the compound, greater than about 95% by weight of one stereoisomer of the compound and less than about 5% by weight of the other stereoisomers of the compound, greater than about 97% by weight of one stereoisomer of the compound and less than about 3% by weight of the other stereoisomers of the compound, greater than about 98% by weight of one stereoisomer of the compound and less than about 2% by weight of the other stereoisomers of the compound or greater than about 99% by weight of one stereoisomer of the compound and less than about 1% by weight of the other stereoisomers of the compound.

As used herein and unless otherwise indicated, the term "stereomerically enriched" means a composition that comprises greater than about 55% by weight of one stereoisomer of a compound, greater than about 60% by weight of one stereoisomer of a compound, greater than about 70% by weight, or greater than about 80% by weight of one stereoisomer of a compound.

In some embodiments, the quinolizidine alkaloid compound is matrine, oxymatrine, or a mixture thereof. Matrine and oxymatrine are both alkaloid compounds found in plants from the *Sophora* genus. As used herein, matrine is a compound having the structure of

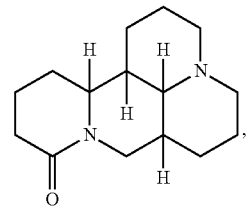

or a pharmaceutically acceptable salt, solvate or stereoisomer thereof. As used herein, oxymatrine is a compound having the structure of

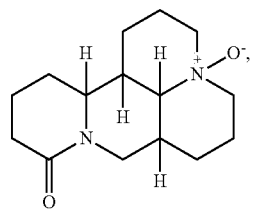

or a pharmaceutically acceptable salt, solvate or stereoisomer thereof. Matrine, oxymatrine, or a mixture thereof may be extracted from a source thereof (such as *Sophora japonica*, *Sophora flavescens*, and *Euchresta japonica* Benth), or may be chemically synthesized. In some embodiments, matrine having the structure of

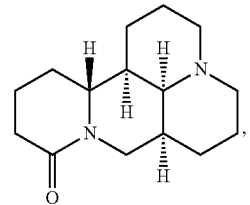

and oxymatrine having the structure of

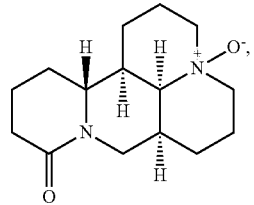

which can be purchased from Sigma-Aldrich®, may be used in compositions provided herein.

In some embodiments, compositions provided herein comprise a source of a quinolizidine alkaloid compound such as a *Sophora* extract. *Sophora* extracts, such as crude herb and crude hot-water extracts, may be obtained from roots and stems of *Sophora flavescens*, by techniques as described herein. Matrine and oxymatrine are believed to be the major bioactive compounds extracted from the root of

*Sophora flavescens* (Yuan et al., Basic Clin Pharmacol Toxicol. 107(5):906-13 (2010).

It is to be understood that extraction from a plant may be performed using conventional techniques such as phenolic extraction, from any part of the plant such as the flower, seed, fruit, root, tubercle, leaf, pericarp and rhizome. The extraction solvents may be chosen from, without limitation, water; propylene glycol, butylene glycol, glycerol, PEG-6 caprylic/capric glycerides, polyethylene glycol, methyl and/or ethyl esters, diglycols, cyclical polyols, ethoxylated or propoxylated diglycols, alcohols (such as methanol, ethanol, propanol, and butanol) and any mixture of these solvents. Plant extracts may also be obtained by other processes such as maceration, simple decoction, lixiviation, reflux extraction, super-critical extraction with $CO_2$, ultrasound or microwave extraction, or counter-current techniques. This list is not restrictive.

In some embodiments, compositions provided herein may comprise a moisturizing agent. Suitable moisturizing agents may comprise allantoin, plant or seed extracts, herbal preparations or combinations thereof that lack toxicity and/or have a protective effect on mucosal membranes. Examples of suitable plant or seed extracts may include, but are not limited to, an extract of rosemary, echinechea, nettle, fennel, juniper, ginseng borage, gelsemium, hamamelis, poke root, arnica, aconite, apis, baptisia, thuja, *aloe*, green tea, nasturtium, bryonia, eupatorium, chamomile, or a mixture thereof. Examples of suitable herbal preparations may include, but are not limited to, an essential oil of red thyme, allspice, cinnamon, savory, or a mixture thereof.

In some embodiments, the moisturizing agent is allantoin. In some embodiments, the moisturizing agent is an *aloe* extract, for example, from *Aloe barbadensis, Aloe vera, Aloe capensis*, or a mixture thereof.

In some embodiments, compositions provided herein may comprise a preservative that lacks toxicity to mucosal membranes. For example, the preservative may comprise methyl paraben, propyl paraben, butyl paraben, or a mixture thereof. In some embodiments, the preservative may comprise (a) methyl paraben; or (b) a mixture of methyl paraben and propyl paraben.

Preservatives that are acceptable for general topical application but may damage cells at mucosal membranes, such as vaginal epithelial cells (VECs), should be avoided. For example, compositions provided herein may not comprise chlorhexidine.

In some embodiments, compositions provided herein may comprise one or more of an excipient, a buffering agent, and a lubricating agent. Excipients, buffering agents and lubricating agents known to those skilled in the art to be safe for application to mucosal membranes may be used. For example, suitable lubricating agents may include, but are not limited to, glycerol; polyethylene glycol (PEG), such as PEG 200 or PEG 400; polypropylene glycol; polyisobutene; polyoxyethylene; behenic acid; behenyl alcohol; sugar-alcohols, such as sorbitol; silicon compounds, such as polydimethyl-siloxane; or a mixture thereof.

It is to be understood that compositions provided herein comprise effective amounts of each ingredient comprised therein. As used herein, an "effective amount" means an amount effective, at dosages and for periods of time necessary, to achieve a desired result. For example, when referring to an octoxynol, an effective amount of the octoxynol may be one that is effective in damaging a microorganism (e.g., damaging the membrane or cell wall of the microorganism), rendering the microorganism unable to infect a subject. In another example, an effective amount of matrine, oxymatrine, or a *Sophora* extract may be one that is effective in protecting cells and normal flora at mucosal membranes.

In some embodiments, compositions provided herein may comprise about 0.05% to about 2.5% (e.g., about 0.1% to about 1%) of an octoxynol on a volume/volume (mL) basis. For example, compositions provided herein may comprise about 0.1% of octoxynol-9 or IGEPAL®CA-630 on a volume/volume (mL) basis.

In some embodiments, compositions provided herein may comprise about 0.2% to about 3% (e.g., about 0.4% to about 2%) of a quinolizidine alkaloid compound, or about 8% to about 30% (e.g., about 15% to about 25%) of a source of the quinolizidine alkaloid compound, on a weight (g)/volume (mL) basis. For example, compositions provided herein may comprise about 0.4% of matrine and/or oxymatrine, or about 20% of a *Sophora* extract from *Sophora flavescens*, on a weight (g)/volume (mL) basis. The amount of a quinolizidine alkaloid compound suitable for compositions provided herein may be from $\frac{1}{50}$ to $\frac{1}{10}$ of the amount of a source of the quinolizidine alkaloid compound suitable for compositions provided herein.

In some embodiments, compositions provided herein may comprise about 0.5% to about 5% (e.g., about 1% to about 2%) of a moisturizing agent on a weight (g)/volume (mL) basis. For example, compositions provided herein may comprise about 0.5% of allantoin or about 2% of an *aloe* extract on a weight (g)/volume (mL) basis.

In some embodiments, compositions provided herein may comprise about 1% to about 5% (e.g., about 1.5% to about 2.5%) of an excipient on a weight (g)/volume (mL) basis. For example, compositions provided herein may comprise about 2% of lactose on a weight (g)/volume (mL) basis.

In some embodiments, compositions provided herein may comprise about 0.1% to about 1% (e.g., about 0.4% to about 0.5%) of a buffering agent on a volume/volume (mL) basis. For example, compositions provided herein may comprise about 0.45% of lactic acid on a volume/volume (mL) basis.

In some embodiments, compositions provided herein may comprise about 2% to about 10% (e.g., about 3% to about 5%) of a lubricating agent on a volume/volume (mL) basis. For example, compositions provided herein may comprise about 3%, about 4%, about 4.5%, or about 5% of glycerol on a volume/volume (mL) basis.

In some embodiments, compositions provided herein may comprise about 0.01% to about 0.2% (e.g., about 0.05% to about 0.15%) of a preservative on a weight (g)/volume (mL) basis. For example, compositions provided herein may comprise about 0.1% of a mixture of methyl paraben and propyl paraben, or a mixture of 0.15% methyl paraben and 0.05% propyl paraben, on a weight (g)/volume (mL) basis.

In some embodiments, compositions provided herein may be formulated in a form that is suitable for application to mucosal membranes, such as a gel or cream. For example, compositions provided herein may be formulated as a gel for vaginal application.

In some embodiments, compositions provided herein may comprise a gelling agent that is known to those skilled in the art to be safe for application to mucosal membranes. Compositions comprising a gelling agent may be suitable for vaginal and/or rectal application, and may also be suitable for application with a prophylactic device such as a condom. Suitable gelling agents may include, but are not limited to, carbomers such as carbomer 980 or 940 NF, 981 or 941 NF, 1382 or 1342 NF, 5984 or 934 NF, ETD 2020, 2050, 934P NF, 971P NF, 974P NF, Noveon AA-1 USP; cellulose derivatives such as ethylcellulose, hydroxypropylmethylcellulose (HPMC), ethylhydroxyethylcellulose (EHEC), carboxymethylcellulose (CMC), hydroxypropylcellulose (HPC), hydroxyethylcellulose (HEC), HPMCP 55; natural gums such as arabic, xanthan, guar gums, alginates; polyvinylpyrrolidone derivatives such as Kollidon grades; polyoxyethylene polyoxypropylene copolymers such as Lutrol F grades 68, 127; chitosan; polyvinyl alcohols; pectins; veegum grades; a tertiary amine, such as triethanolamine or trolamine; or a mixture thereof. In some embodiments, the gelling agent is HEC.

In some embodiments, compositions provided herein may comprise about 1% to about 8% (e.g., about 2.5% to about 7%) of a gelling agent on a weight (g)/volume (mL) basis. For example, compositions provided herein may comprise about 2.5% or about 5% of HEC on a weight (g)/volume (mL) basis.

Compositions provided herein can be prepared by any of the methods of pharmacy. In general, compositions provided may be are prepared by uniformly admixing (e.g., direct blend) the ingredients. An exemplary process of making a gel that is suitable for vaginal application according to the present invention is illustrated in FIG. 1. The steps in FIG. 1 may be carried out in a standard bioreactor.

Compositions provided herein may have a pH in the acidic range, for example between about 4.5 and about 5.6. In some embodiments, compositions provided herein may have a pH of about 5.0. Compositions provided herein may have a viscosity between about 30 PaS and about 50 PaS. Compositions provided herein may adhere to mucosal membranes, such as vaginal epithelium, for a sufficient period of time for killing STD-causing microorganisms and/or sperms.

Kits

The present invention may be provided to a user as a kit. For example, a kit of the invention contains one or more of the compositions provided herein.

In some embodiments, kits provided herein may comprise an applicator for applying or administering compositions to mucosal membranes of a subject, such as the vagina of a human female. Suitable applicators may include, but are not limited to a wipe, a measuring cup, a douche, an enema, a syringe, a tampon, a spray or a mixture thereof.

In some embodiments, kits provided herein may comprise a prophylactic device. Compositions provided herein may be carried on, coated on, or impregnated into, one or more surfaces of the prophylactic device. Alternately, compositions provided herein may be administered separately from the prophylactic device. The prophylactic device may be of any suitable type. A condom, cervical cap, contraceptive diaphragm, vaginal sponge, intrauterine device, pessary or the like may be used.

In some embodiments, kits provided herein may further comprise one or more additional reagents, packaging material, containers for holding the components of the kit, and an instruction set or user manual detailing preferred methods of using the kit components.

Methods

Compositions and/or kits provided herein may be useful for prevention of conception and/or prevention of transmission of STDs. It is to be understood that "prevention" as referenced in methods provided herein is intended to mean at least the reduction in incidence or prevalence of the occurrence of the specified activity relative to an untreated subject. This term may further refer to reduced transmission of STD infection and/or conception as a result of administration of compositions provided herein to a subject prior to, or immediately after, intimate contact relative to untreated subjects.

By "administering/administration" or "applying/application," it is meant that a composition is delivered to a subject in such a way that it can achieve a desired purpose. The amount of compositions administered may vary depending upon factors such as the STD-causing microorganism intended to be inhibited.

Accordingly, methods provided herein may comprise administering or applying compositions provided herein to the vulva, including the vaginal cavity, the penis and the ano-rectal and buccal cavities by contacting the skin or mucosal membranes of a site of infection or likely infection or surrounding the site of infection or likely infection. The mucosal or skin surface may further include the perianal, and the lining of the anus.

The site of infection may be one where an infection is already present (an actual site of infection) or where an infection is likely to occur (a potential site of infection in or on an uninfected individual).

In some embodiments, methods provided herein may comprise administering or applying compositions provided herein to external genitalia and/or internal mucosal surfaces to prevent transmission of viable STD-causing microorganisms through traumatized, diseased or healthy skin or mucosa. For example, compositions provided herein may be discharged into the vagina of a human female.

In some embodiments, methods provided herein may comprise administering or applying compositions provided herein indirectly or directly to a subject in need thereof. This may be done, for example, by applying compositions provided herein onto or into the vaginal area or indirectly by applying compositions provided herein onto a prophylactic device.

In some embodiments, methods provided herein may comprise administering or applying compositions provided herein so as to decrease the possibility of sperm-egg fertilization, either by blocking entry of sperm into the egg, inhibiting sperm-fertilizing capabilities or by other methods.

EMBODIMENTS

Particular embodiments of the invention include, without limitation, the following:

1. A composition comprising (a) an octoxynol; and (b) a quinolizidine alkaloid compound or a source thereof, wherein the quinolizidine alkaloid compound has a structure:

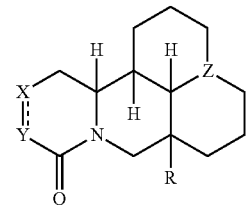

or a pharmaceutically acceptable salt, solvate or stereoisomer thereof, wherein:
R is H or OH;
X and Y are each CH2 or CH; and
Z is N or NO.

2. The composition of paragraph 1, wherein the octoxynol is an ethoxylated alkylphenol chosen from octoxynol-1, octoxynol-3, octoxynol-5, octoxynol-6, octoxynol-7, octoxynol-8, octoxynol-9, octoxynol-10, octoxynol-11, octoxynol-12, octoxynol-13, octoxynol-16, octoxynol-20, octoxynol-25, octoxynol-30, octoxynol-33, octoxynol-40, octoxynol-70, octoxynol-9 carboxylic acid, octoxynol-20 carboxylic acid, potassium octoxynol-12 phosphate, sodium octoxynol-2 ethane sulfonate, sodium octoxynol-2 sulfate, sodium octoxynol-6 sulfate, sodium octoxynol-9 sulfate, IGEPAOCA-630 and a mixture thereof.

3. The composition of paragraph 1 or 2, wherein the octoxynol is octoxynol-9.

4. The composition of paragraph 1 or 2, wherein the octoxynol is IGEPAL®CA-630.

5. The composition of any one of paragraphs 1 to 4, wherein the quinolizidine alkaloid compound is matrine and/or oxymatrine.

6. The composition of any one of paragraphs 1 to 5, wherein the source of the quinolizidine alkaloid compound is a *Sophora* extract.

7. The composition of paragraph 6, wherein the *Sophora* extract is from *Sophora flavescens*.

8. The composition of paragraph 7, wherein the *Sophora* extract is from roots of *Sophora* flavescens.

9. The composition of paragraph 7, wherein the *Sophora* extract is from stems of *Sophora flavescens*.

10. The composition of any one of paragraphs 1 to 9 further comprising a moisturizing agent.

11. The composition of paragraph 10, wherein the moisturizing agent is chosen from allantoin; an extract of rosemary, echinechea, nettle, fennel, juniper, ginseng borage, gelsemium, hamamelis, poke root, arnica, aconite, apis, baptisia, thuja, *aloe*, green tea, nasturtium, bryonia, eupatorium, chamomile, or a mixture thereof; an essential oil of red thyme, allspice, cinnamon, savory, or a mixture thereof; and a mixture thereof.

12. The composition of paragraph 10 or 11, wherein the moisturizing agent is an *aloe* extract.

13. The composition of any one of paragraphs 10 to 12, wherein the moisturizing agent is an *aloe* extract from *Aloe barbadensis*, *Aloe vera*, *Aloe capensis*, or a mixture thereof.

14. The composition of paragraph 10 or 11, wherein the moisturizing agent is allantoin.

15. The composition of any one of paragraphs 10 to 14 comprising about 0.5% to about 5% of the moisturizing agent on a weight (g)/volume (mL) basis.

16. The composition of any one of paragraphs 1 to 15 further comprising a preservative.

17. The composition of paragraph 16, wherein the preservative comprises methyl paraben, propyl paraben, butyl paraben, or a mixture thereof.

18. The composition of paragraph 16 or 17, wherein the preservative comprises a mixture of methyl paraben and propyl paraben.

19. The composition of any one of paragraphs 1 to 18 comprising about 0.05% to about 2.5% of the octoxynol, on a volume/volume (mL) basis, and about 0.2% to about 3% of the quinolizidine alkaloid compound, or about 8% to about 30% of the source of the quinolizidine alkaloid compound, on a weight (g)/volume (mL) basis.

20. The composition of any one of paragraph 1 to 19 further comprising one or more of an excipient, a buffering agent, and a lubricating agent.

21. The composition of paragraph 20, wherein the lubricating agent is chosen from glycerol; polyethylene glycol (PEG), such as PEG 200 or PEG 400; polypropylene glycol; polyisobutene; polyoxyethylene; behenic acid; behenyl alcohol; sugar-alcohols, such as sorbitol; silicon compounds, such as polydimethyl-siloxane; and a mixture thereof.

22. The composition of any one of paragraphs 1 to 21 which is formulated as a gel.

23. The composition of paragraph 22 comprising a gelling agent.

24. The composition of paragraph 23, wherein the gelling agent is chosen from carbomer 980 or 940 NF, 981 or 941 NF, 1382 or 1342 NF, 5984 or 934 NF, ETD 2020, 2050, 934P NF, 971P NF, 974P NF, Noveon AA-1 USP; cellulose derivatives such as ethylcellulose, hydroxypropylmethylcellulose (HPMC), ethylhydroxyethylcellulose (EHEC), carboxymethylcellulose (CMC), hydroxypropylcellulose (HPC), hydroxyethylcellulose (HEC), HPMCP 55; natural gums such as arabic, xanthan, guar gums, alginates; polyvinylpyrrolidone derivatives such as Kollidon grades; polyoxyethylene polyoxypropylene copolymers such as Lutrol F grades 68, 127; chitosan; polyvinyl alcohols; pectins; veegum grades; a tertiary amine, such as triethanolamine or trolamine; and a mixture thereof.

25. A composition comprising octoxynol-9 and a *Sophora* extract from *Sophora flavescens*.

26. The composition of paragraph 25 comprising about 8% to about 30% of the *Sophora* extract on a weight (g)/volume (mL) basis.

27. The composition of paragraph 25 or 26 further comprising about 0.5% to about 5% of an *aloe* extract on a weight (g)/volume (mL) basis.

28. A composition comprising IGEPAL®CA-630 and matrine and/or oxymatrine.

29. The composition of claim 28 comprising about 0.2% to about 3% of matrine on a weight (g)/volume (mL) basis.

30. The composition of paragraph 28 or 29 further comprising about 0.5% to about 5% of allantoin on a weight (g)/volume (mL) basis.

31. The composition of any one of paragraphs 25 to 30 further comprising a preservative.

32. The composition of paragraph 31, wherein the preservative comprises a mixture of methyl paraben and propyl paraben.

33. The composition of any one of paragraphs 25 to 32 further comprising one or more of an excipient, a buffering agent, and a lubricating agent.

34. The composition of any one of paragraphs 25 to 32 further comprising an excipient, a buffering agent, and a lubricating agent.

35. The composition of paragraph 33 or 34, wherein the excipient is lactose.

36. The composition of any one of paragraphs 33 to 35, wherein the buffering agent is lactic acid.

37. The composition of any one of paragraphs 33 to 36, wherein the lubricating agent is glycerol.

38. The composition of any one of paragraphs 33 to 37 further comprising a gelling agent.

39. The composition of claim 38, wherein the gelling agent is hydroxyethylcellulose (HEC).

40. The composition of any one of paragraphs 25 to 39 comprising about 0.05% to about 2.5% of octoxynol-9 or IGEPAL®CA-630 on a volume/volume (mL) basis.

41. A composition comprising:
about 0.05% to about 2.5% of octoxynol-9 on a volume/volume (mL) basis;
about 8% to about 30% of a *Sophora* extract, on a weight (g)/volume (mL) basis;
about 0.5% to about 5% of an *aloe* extract on a weight (g)/volume (mL) basis;
about 3% to about 5% of glycerol on a volume/volume (mL) basis;

about 1% to about 8% of HEC on a weight (g)/volume (mL) basis; and optionally, about 0.01% to about 0.2% of a mixture of methyl paraben and propyl paraben on a weight (g)/volume (mL) basis.

42. A composition comprising:
about 0.05% to about 2.5% of IGEPAL®CA-630 on a volume/volume (mL) basis;
about 0.2% to about 3% of matrine and/or oxymatrine;
about 0.5% to about 5% of allantoin on a weight (g)/volume (mL) basis;
about 3% to about 5% of glycerol on a volume/volume (mL) basis;
about 1% to about 8% of HEC on a weight (g)/volume (mL) basis; and
optionally, about 0.01% to about 0.2% of a mixture of methyl paraben and propyl paraben on a weight (g)/volume (mL) basis.

43. A composition comprising:
about 0.1% of octoxynol-9 on a volume/volume (mL) basis;
about 20% of a *Sophora* extract, on a weight (g)/volume (mL) basis;
about 2% of an *aloe* extract on a weight (g)/volume (mL) basis;
about 5% of glycerol on a volume/volume (mL) basis;
about 5% of HEC on a weight (g)/volume (mL) basis; and
optionally, about 0.1% of a mixture of methyl paraben and propyl paraben on a weight (g)/volume (mL) basis.

44. A composition comprising:
about 0.1% of IGEPAL®CA-630 on a volume/volume (mL) basis;
about 0.4% of matrine;
about 0.5% of allantoin on a weight (g)/volume (mL) basis;
about 4% of glycerol on a volume/volume (mL) basis;
about 2.5% of HEC on a weight (g)/volume (mL) basis; and
optionally, a mixture of about 0.15% of methyl paraben and about 0.05% of propyl paraben on a weight (g)/volume (mL) basis.

45. The composition of paragraph 41 or 43, wherein the *Sophora* extract is from *Sophora flavescens*.

46. The composition of paragraph 45, wherein the *Sophora* extract is from roots of *Sophora* flavescens.

47. The composition of paragraph 45, wherein the *Sophora* extract is from stems of *Sophora flavescens*.

48. The composition of any one of paragraphs 1 to 47 having a pH between about 4.5 and about 5.6.

49. The composition of any one of paragraphs 1 to 48 having a viscosity between about 30 PaS and about 50 PaS.

50. The composition of any one of paragraphs 1 to 49 for use in prevention of conception and/or prevention against transmission of a sexually transmitted disease.

51. The composition of paragraph 50, wherein the sexually transmitted disease is HIV/AIDS, herpes simplex types 1 and 2, gonorrhea, *chlamydia*, trichomoniasis, or a mixture thereof.

52. A method of prevention of conception and/or prevention of transmission of a sexually transmitted disease, said method comprising administering the composition of any one of paragraphs 1 to 49 to a subject.

53. The method of paragraph 52, wherein the subject is a human female.

54. The method of paragraph 53, wherein the administration comprises discharging the composition of any one of paragraphs 1 to 49 into the vagina or anus of the human female.

55. The method of paragraph 52, wherein the subject is a human male.

56. The method of paragraph 55, wherein the administration comprises discharging the composition of any one of paragraphs 1 to 49 into the anus of the human male.

57. A method of prevention of conception and/or prevention of transmission of a sexually transmitted disease, said method comprising discharging the composition of any one of paragraphs 1 to 49 into the vagina of a human female.

58. The method of any one of paragraphs 52 to 57, wherein the sexually transmitted disease is HIV/AIDS, herpes simplex types 1 and 2, gonorrhea, *chlamydia*, or trichomoniasis.

59. A kit for prevention of conception and/or prevention of transmission of a sexually transmitted disease comprising:
a. the composition of any one of paragraphs 1 to 49;
b. an applicator; and
c. optionally a prophylactic device.

60. The kit of paragraph 59, wherein the sexually transmitted disease is HIV/AIDS, herpes simplex types 1 and 2, gonorrhea, *chlamydia*, or trichomoniasis.

61. The kit of any one of paragraphs 59 or 60, wherein the applicator is chosen from a wipe, a measuring cup, a douche, an enema, a syringe, a tampon, a spray and a mixture thereof.

62. The kit of any one of paragraphs 59 to 61, wherein the prophylactic device is choose from a condom, a cervical cap, a contraceptive diaphragm, a vaginal sponge, an intrauterine device, a pessary and a mixture thereof.

EXAMPLES

Example 1: Toxicity on Vaginal Epithelial Cells

Materials

VK2, Ect1 and End1 are transformed human genital epithelial cell lines corresponding to vagina, ectocervix and endocervix. These cell lines were obtained from ATCC, USA.

Formulation A tested contains 0.1% of octoxynol-9 (mL/mL), 20% of a *Sophora* extract from *Sophora flavescens* (g/mL), 2% of an *aloe* extract (g/mL), 2% of lactose (g/mL), 0.45% of lactic acid (mL/mL), 5% glycerol (mL/mL), and 5% HEC (g/mL). Formulation B tested has all the ingredients of Formulation A and 0.1% of a mixture of methyl paraben and propyl paraben (g/mL). Formulation C tested contains 60% of a *Sophora* extract from *Sophora flavescens* (g/mL), 2% of an *aloe* extract (g/mL), 2% of lactose (g/mL), 5% glycerol (mL/mL), and 5% HEC (g/mL).

Experimental Procedure

1. $2 \times 10^4$ VK2, Ect1 or End1 cells were seeded into each well of 96-well plates.

2. After 24 hrs culture, when epithelial cells formed uniform monolayers, serial dilutions of the formulations were added. Each dilution was in triplicate.

3. After 24 hrs, 10 µL CCK-8 working solution (CCK8 (Cell Counting Kit-8)
Code: CK04. Lot.FH727. Dojindo Laboratories. Dojindo, Kumamoto, Japan) was dispensed into each well, and then the plates were incubated at 37° C., 5% $CO_2$ for 4 hrs.

4. The absorbance at 460 nm was measured using a TECAN™ Fluorometer (TECAN Fluorometer. Infinite M200. Device serial number: M200 Nano Quant. Equipment type: 912004494. Switzerland).

Results

Figure 2A:
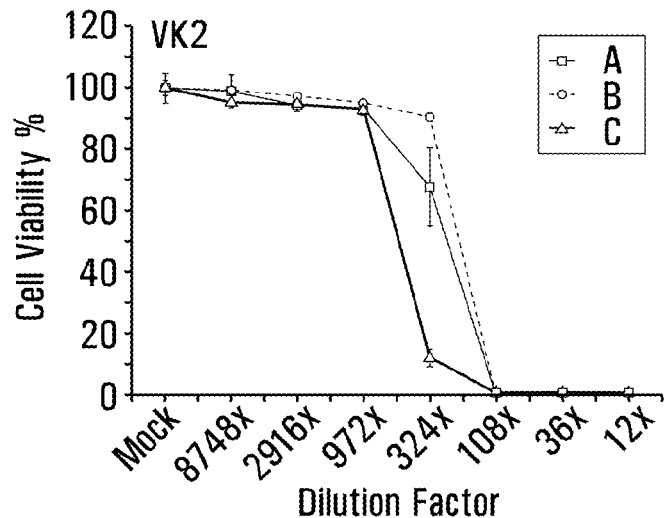
FIGS. 2A to 2C show the effect of Formulations A to C on cell viability of three VEC lines.
Figure 2B:
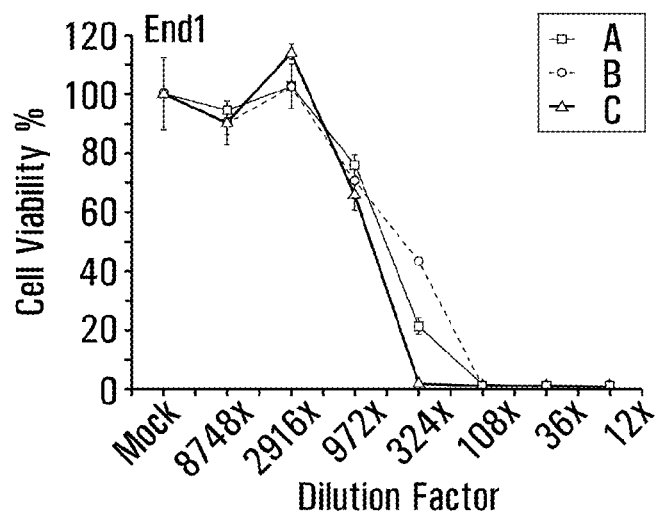
Figure 2C:
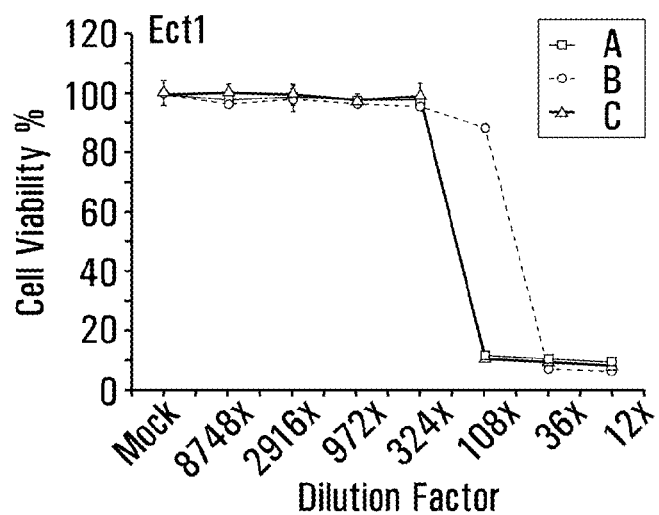
Figure 3A:
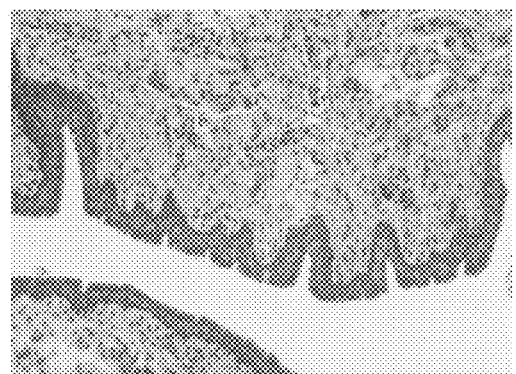
FIGS. 3A to 3E are representative microscopic pictures of the ectocervixes and/or vaginas of the rabbits treated with different formulations.
Figure 3B:
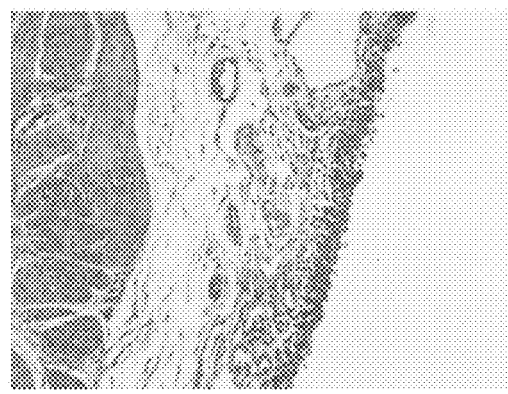
Figure 3C:
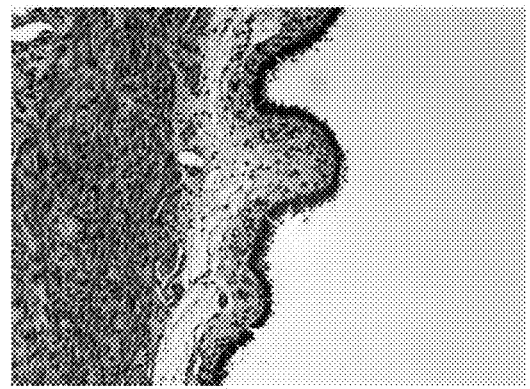
Figure 3D:
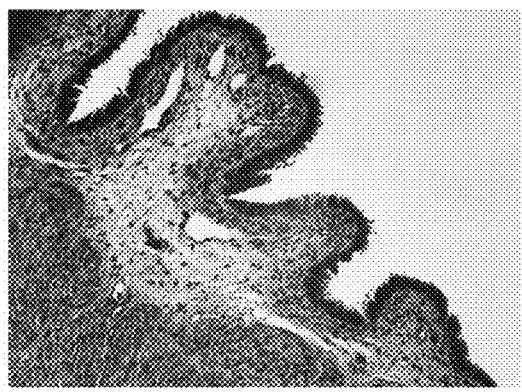
Figure 3E:
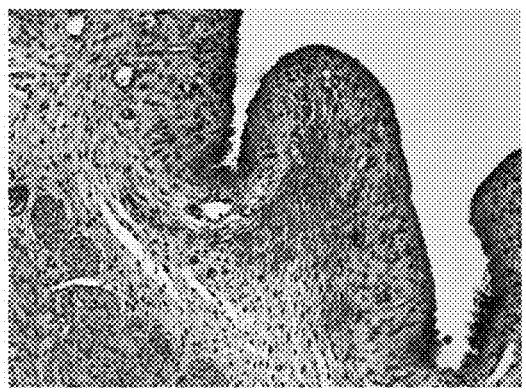

As shown in FIGS. 2A to 2C, the minimum dilution factors of Formulations A to C resulting 100% cell killing ranged from 36× to 324×, which are higher than that of a formulation containing chlorhexidine (dilution factor of 1620×; not shown). Formulation C appeared to be slightly more toxic than Formulations A and B.

Except in End1 cells, the cytotoxicity of Formulations A to C lacked a dose-dependent relationship and exhibited a sharp increase in cytotoxicity when the dilutions reached a critical point.

Example 2: Vaginal Irritation Study

Materials

Mature big ear female rabbits (body weight: 2 kg) were provided by Nanjing Qinglongshan animal breeding Facility (qualification license: SCXK(Su)2007-0001). The rabbits were adapted to the environment for one week before the experiment. Formulations A to C identified in Example 1 were tested. Phosphate saline was used as blank and HEC gel purchased from Sigma-Aldrich was used as negative control.

Experimental Procedure

1. Treatment

Before the experiment, the rabbits were stimulated to urinate using disposable catheter. The animals were then treated with the formulations which were administered through disposable catheter (Sterile catheter Disposable. Jiangsu Huatai Medical Devices Co., Ltd. Type: Fr12. Batch No: 20130709) which was inserted 7 cm into vagina. 1 mL or 2 mL of the formulation was administered each treatment, twice per day at 8:30 and 15:30, respectively. The treatment was continued for 7 days.

2. Group

Animals were divided into groups according to the formulations administered. Phosphate saline mechanical stimulation was the control group.

3. Tissue Examination

Daily observation was performed on the vagina and the animals were sacrificed on day 8, and various tissue samples were prepared. The tissues were treated in 0.9% phosphate saline for 30 sec, and after fixed in 10% neutral buffered formalin, the tissues were dehydrated, imbedded in paraffin, sectioned to 4 μm and stained with hematoxylin and eosin (HE). The sections were examined under optical microscope.

4. Scoring of Vaginal Irritation

The tissue sections were scored using Eckstein Irritation Scores (see: Eckstein P, Jackson M C, Millman N, Sobrero A J (1969) Comparison of vaginal tolerance tests of spermicidal preparations in rabbits and monkeys. J Reprod Fertil 20:85-93). Scores were given to hyperemia, edema, inflammatory cell infiltration and epithelial exuviations separately. Score of individual parameters was from low to high as following: 0 representing no irritation and 4 representing severe irritation. A total combined score of less than 4 represents minimal irritation, 5-8 mild irritation, 9-12 medium irritation and 13-16 severe irritation. A total score of 0-8 means irritation is acceptable, 9-10 marginal and 11 or higher than 11 unacceptable.

Results

Ectocervix and vagina were examined and no hyperemia, inflammation, abnormal vaginal discharge were observed. No apparent anatomic abnormality was observed after the animal tissues were dissected. Microscopic structures, such as epithelium, were intact.

The scores for different treatments are shown in Table 1. Representative microscopic pictures are shown in FIGS. 3A to 3E.

TABLE 1

Vaginal Irritation Scores

| Group | Infiltration | Epithelial ulceration | Hyperemia | Edema | Total Score |
|---|---|---|---|---|---|
| Phosphase Saline | 0 | 0 | 0 | 0 | 0 |
|  | 0 | 0 | 0 | 0 | 0 |
|  | 1 | 0 | 1 | 0 | 2 |
|  | 0 | 0 | 0 | 0 | 0 |
| Negative Control | 0 | 2 | 0 | 0 | 2 |
|  | 0 | 1 | 2 | 0 | 3 |
|  | 1 | 1 | 3 | 2 | 7 |
|  | 1 | 1 | 3 | 2 | 7 |
| Formulation A (2 mL) | 0 | 0 | 1 | 3 | 4 |
|  | 1 | 0 | 0 | 2 | 3 |
|  | 1 | 0 | 1 | 2 | 4 |
|  | 0 | 0 | 1 | 1 | 2 |
|  | 0 | 0 | 0 | 1 | 1 |
|  | 1 | 1 | 1 | 2 | 5 |
| Formulation B (2 mL) | 1 | 2 | 3 | 3 | 9 |
|  | 1 | 3 | 3 | 3 | 10 |
|  | 1 | 2 | 2 | 1 | 6 |
|  | 0 | 0 | 1 | 2 | 3 |
|  | 1 | 0 | 1 | 2 | 4 |
|  | 1 | 0 | 1 | 1 | 3 |
| Formulation C (2 mL) | 2 | 0 | 3 | 1 | 6 |
|  | 2 | 1 | 3 | 2 | 8 |
|  | 2 | 1 | 3 | 2 | 8 |
|  | 3 | 3 | 4 | 4 | 14 |
|  | 4 | 3 | 4 | 4 | 15 |
|  | 4 | 3 | 4 | 4 | 15 |

Formulations A and B did not cause inflammatory cell infiltration, epithelial lesion, hyperemia or edema on the vaginal epithelium and showed no significant differences whether the formulation contains methyl paraben. Formulation C induced inflammatory cell infiltration, epithelial ulceration, hyperemia and edema and resulted in unacceptable levels of irritation.

Example 3: Examination of Vaginal Flora

Materials 6 wild type *Lactobacillus* samples were collected from healthy female subjects. The strain of *Lactobacillus acidophilus* was purchased ATCC (Cat No. 4356). Formulations A and B identified in Example 1 were tested. A commercial nonoxynol-9 (N9) gel, namely, Conceptrol manufactured by Ortho, USA, was used as reference.

Results

Figure 4:
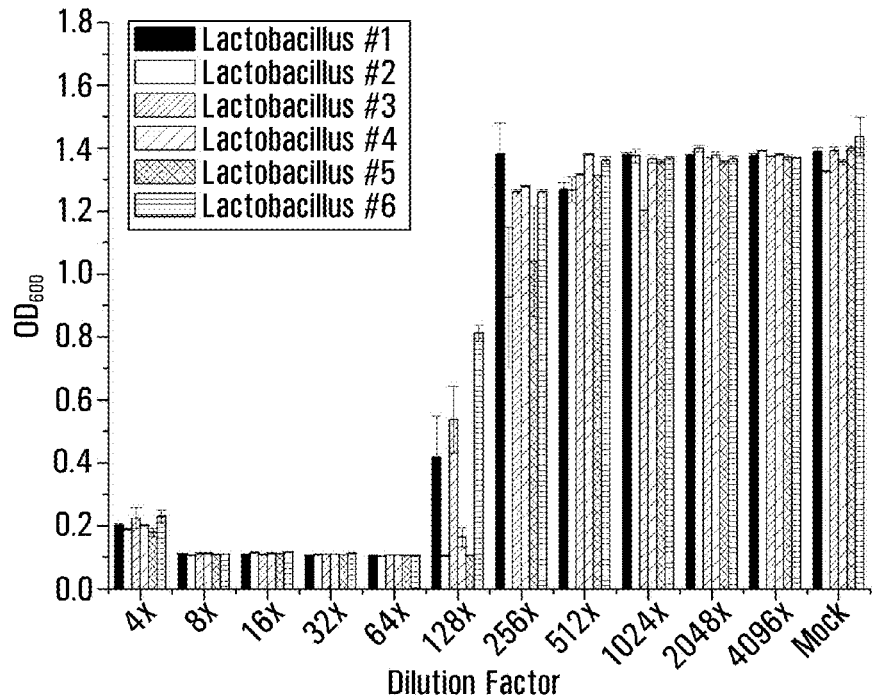
FIG. 4 shows the effect of Formulation B on vaginal *Lactobacillus*. The error bars represent standard deviations (±SD).
Figure 5:
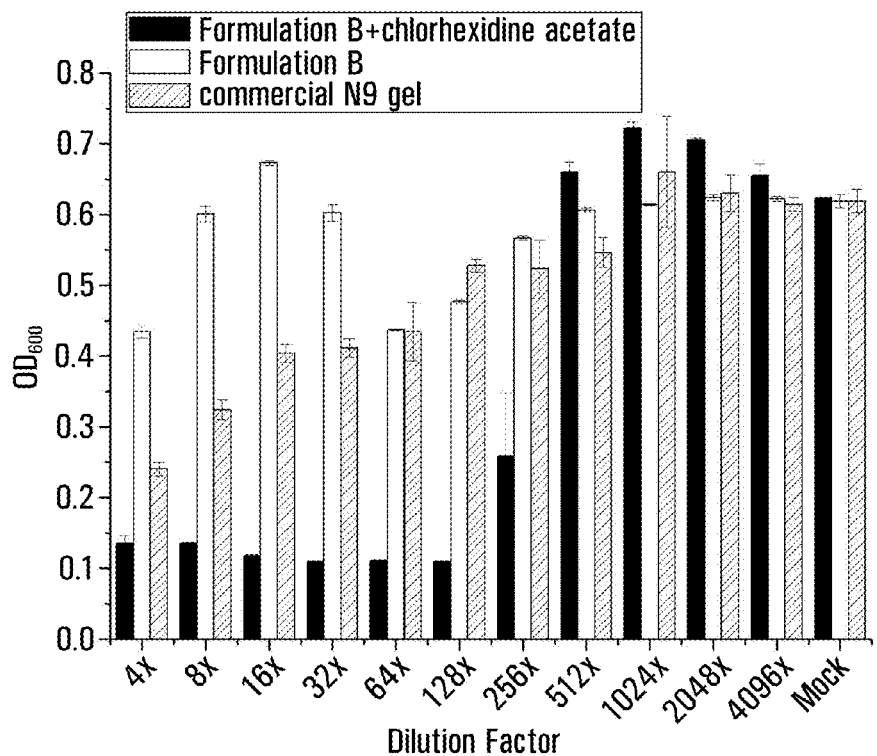
FIG. 5 shows the effects of various formulations on vaginal *Lactobacillus*. The error bars represent standard deviations (±SD). The different dilutions of the commercial N9 gel have 7.5, 3.75, 1.88, 0.94, 0.47, 0.23, 0.12, 0.059, 0.029, 0.015, 0.007 mg/mL of nonoxynol-9.
Figure 6:
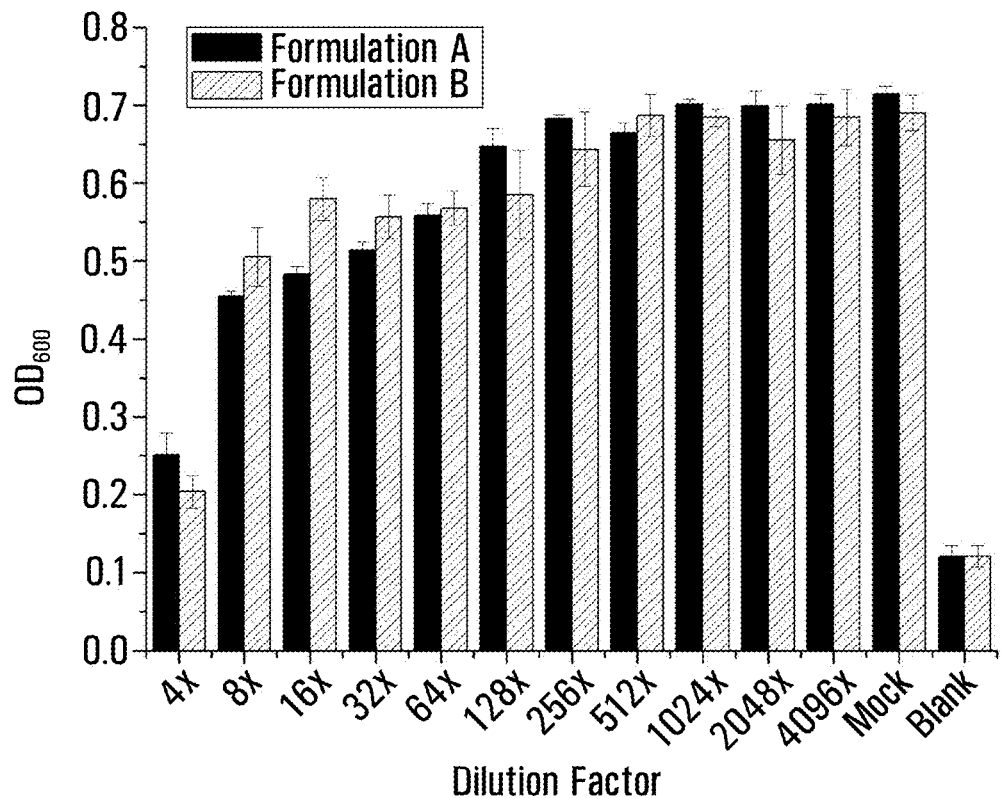
FIG. 6 shows the effects of Formulations A and B on vaginal *Lactobacillus*. The error bars represent standard deviations (±SD).

Formulation A was tested on the 6 wild type *Lactobacillus* samples and the results were shown in FIG. 4. Formulation B without and with chlorhexidine acetate and the commercial N9 gel were tested and the results were shown in FIG. 5. Formulations A and B were tested on the ATCC strain of *Lactobacillus acidophilus* and the results were shown in FIG. 6.

Example 4: Examination of Vaginal pH

Materials

Formulation B identified in Example 1 was tested. PBS was used as control.

Experimental Procedure 6 female rabbits (2 kg) were randomly divided into 2 groups (3 in control group, 3 in treatment group). The rabbits' vaginas were washed using 1 mL PBS or 1 mL. Formulation B, and the discharges were collected for pH measurement. Vaginal stimulation urination proceeded before administration of PBS or Formulation B.

Results

Formulation B did not significantly modify the pH of the vaginal discharges.

Example 5: Toxicity on Ghost Cells

Materials

Ghost R5X4 cells were obtained from Tissue Culture Repository, Chinese Academy of Sciences, Beijing, China. This cell line served as the indicator cell for anti-HIV analysis. Formulation B identified in Example 1 was tested using experimental procedure 5A and Formulations A to C identified in Example 1 were tested using experimental procedure 5B.

Experimental Procedure

5A:
1. Serial dilutions of Formulation B were added to 96-well plates. $1 \times 10^4$ Ghost cells/well were then added. Each dilution was in triplicate.
2. The cells were cultured at 37° C. for 48 hours.
3. Part of the culture media was removed to retain 100 μL/well. 5 μL CCK8 solution was added and the plates were incubated at 37° C. for 2 hours.
4. OD values were measured at 450 nm.
5. Cell viability was calculated according to: Cell viability=$OD_{450}$ sample/$OD_{450}$ control (untreated cells).
5B: see the experimental procedure identified in Example 1

Results

Figure 7:
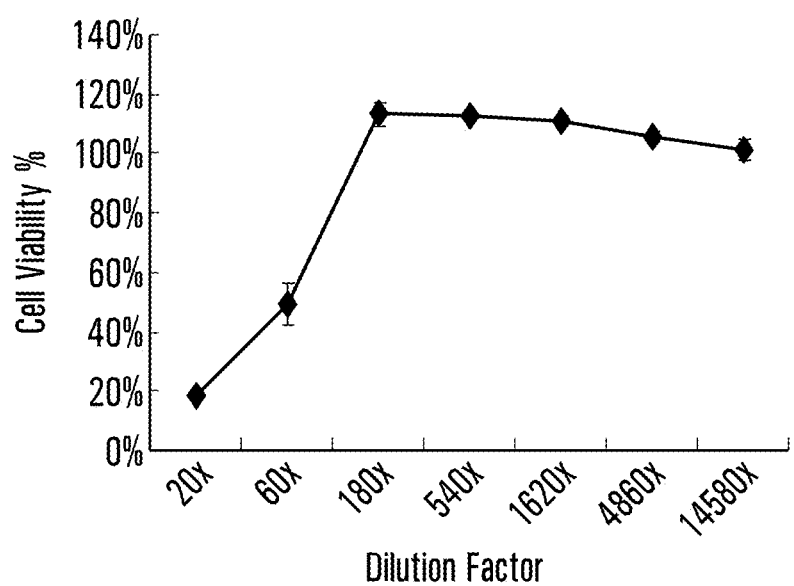
FIG. 7 shows the effect of Formulation B on cell viability of Ghost cells. The error bars represent standard deviations (±SD).
Figure 8:
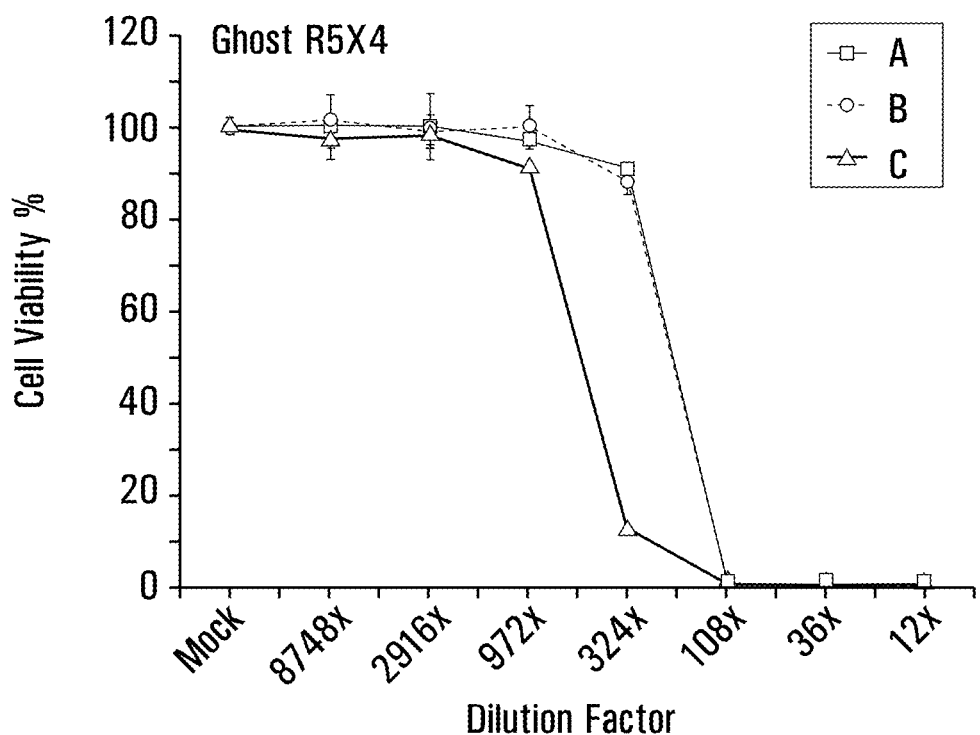
FIG. 8 shows the effects of Formulations A to C on cell viability of Ghost cells. The error bars represent standard deviations (±SD).

The results of experimental procedure 5A were shown in FIG. 7. When Formulation B was used at dilution factors at or higher than 180×, no cytotoxicity was observed. The 50% cytotoxicity of Formulation B was estimated to be at a dilution factor between 120× and 150×. The results of experimental procedure 5B were shown in FIG. 8.

Example 6: Anti-HIV-1 Activity

Materials

Formulations A to C identified in Example 1 were tested using experimental procedure 6A; and Formulation B identified in Example 1 was tested using experimental procedure 6B to 6D; and Formulations A and B identified in Example 1 were tested using experimental procedure 6E.

Experimental Procedure

CNE33 is a CCR5-using clinical isolate (a subtype BC recombinant HIV-1 (CRF) isolated from a Chinese patient, obtained by Prof. Hong Shang, China Medical University, Shengyang. China). The infectivity assay used is a standard, high sensitivity pseudoviral infectivity assay that measures luciferase output controlled by viral long terminal repeat (LTR), which is approximately 640 bp in length and is a control block for viral gene expression during HIV replication cycle (Qiu M et al. (2012) PLoS ONE 7(4): e35906.doi: 10.1371/journal.pone.0035906; Qiu M et al. (2012) Antiviral Research 96(2):138-147).

Semen were collected from several healthy individuals from hospital clinics affiliated with Nanjing University School of Medicine, and after initial screening, three of the samples met the criteria (such as mobility, semen counts, free of other infections).

6A:
1. $2 \times 10^4$ Ghost R5X4 cells were seeded into each well of 96-well plates.
2. After 24 hrs culture, CNE33 pseudotyped virus stocks were mixed with serial dilutions of the formulations at a ratio of 1:1. Each dilution was in triplicate.
3. After 30 min incubation, the mixtures were diluted to 80× with culture media (DMEM/10% FBS).
4. 50 μL of the dilutions was dispensed to each well.
5. After 48 hrs culture in a 37° C., 5% $CO_2$ incubator, the luciferase activity was measured.

6B:
1. Formulation B was incubated 4× dilution with CNE33 at 37° C. for 5, 10, and 15 min, respectively. Mock wells contained culture media instead of Formulation B, and was incubated at 37° C. for 15 min;
2. 50 μL mixture was removed and diluted to contain 4000TCID50/mL CNE33 and then added to $1 \times 10^4$ Ghost cells/well;
3. After 48 hrs culture at 37° C., fluorescence was measured.

6C: Serial dilutions of Formulation B were incubated with CNE33 at 37° C. for 5 min and the remaining steps of 6B were repeated.

6D: In Formulation B only treatment (N), various dilutions of Formulation B, cultural media and virus were mixed at 1:1:1 volume ratio; in Formulation B+semen treatment (N+S), various dilutions of Formulation B, semen and virus were mixed at 1:1:1 volume ratio. The mixtures were incubated at 37° C. for 5 min and the remaining steps of 6B were repeated.

6E:
1. $2 \times 10^4$ cells/well Ghost R5X4 cells were seeded on 96-well cultural plates and the cells were cultured in a 5% $CO_2$, 37° C. culture incubator for 24 hrs to reach 90% confluence.
2. Formulations A or B were added at the dilution factor of 324× and the cells were treated for 30 min.
3. After 30 min, the formulations were removed from one of the plates and the cells were washed once with culture medium and another plate was allowed to remain in the formulations.
4. The cells in both plates were infected with CNE33 pseudotyped virus stocks at a high inoculum of 4000TCID50/mL and the infection was allowed for 48 hrs.
5. The luciferase activity was measured.

Results

Figure 9:
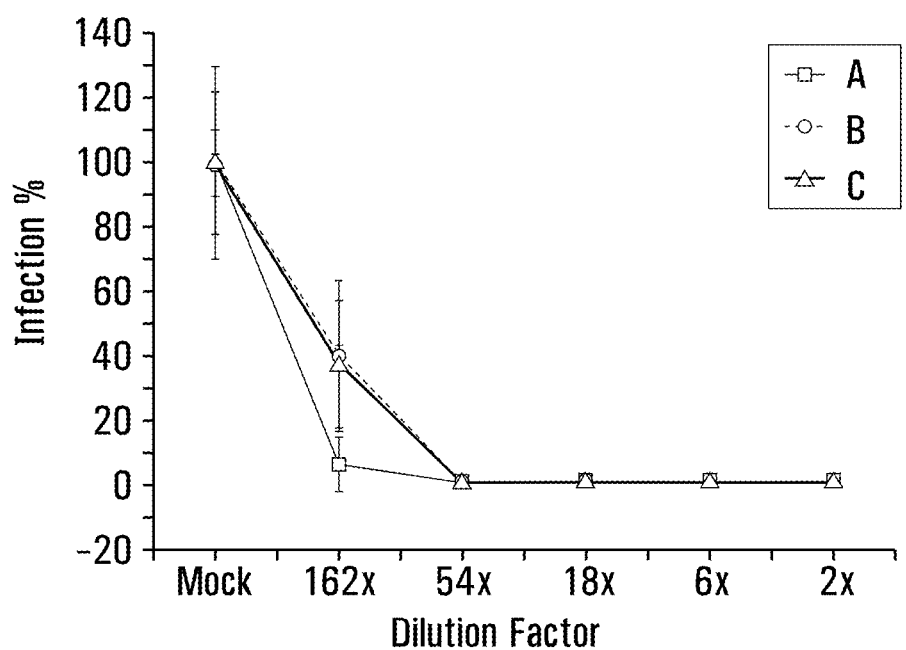
FIG. 9 shows the anti-HIV-1 activities of Formulations A to C. The error bars represent standard deviations (±SD).
Figure 10:
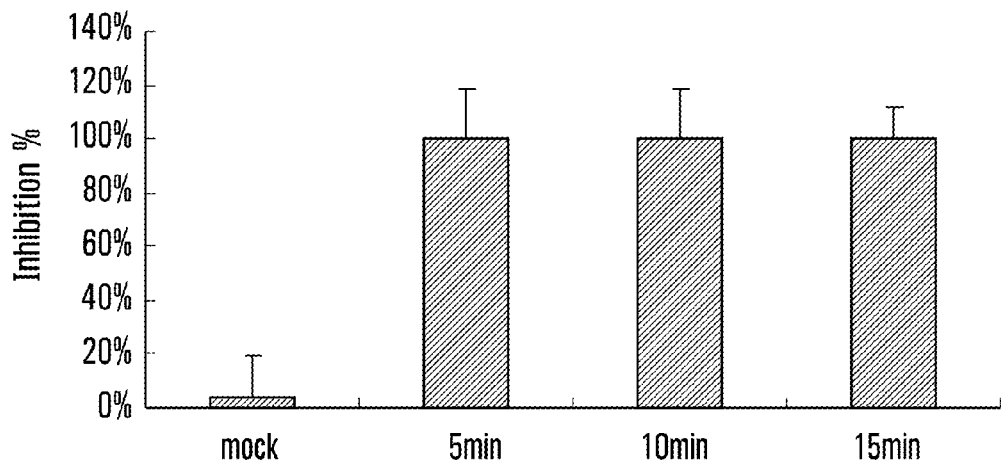
FIG. 10 shows the anti-HIV-1 activities of Formulation B tested at different time points. The error bars represent standard deviations (±SD).
Figure 11:
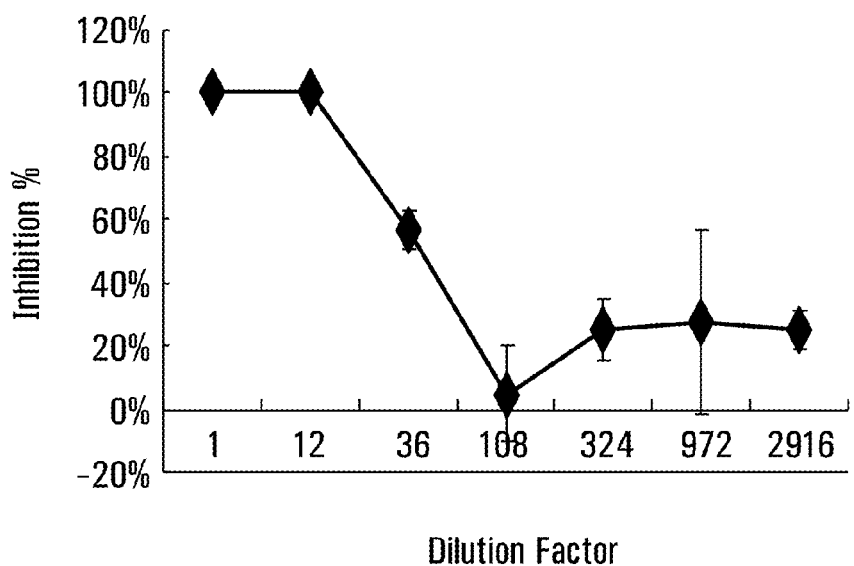
FIG. 11 shows the anti-HIV-1 activities of serial dilutions of Formulation B. The error bars represent standard deviations (±SD).
Figure 12:
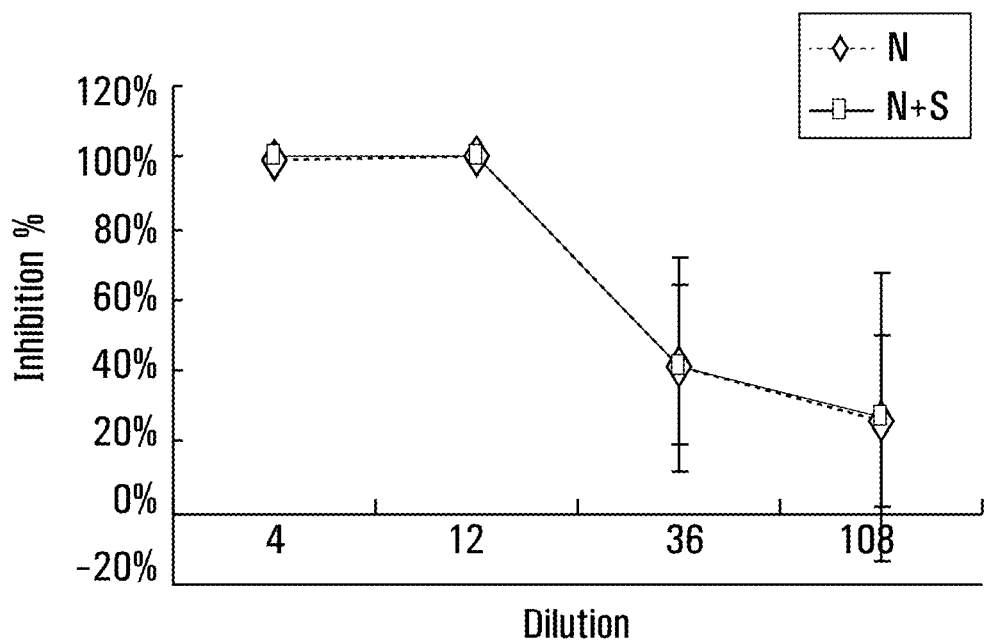
FIG. 12 shows the anti-HIV-1 activities of Formulation B with or without human semen. The error bars represent standard deviations (±SD).
Figure 13:
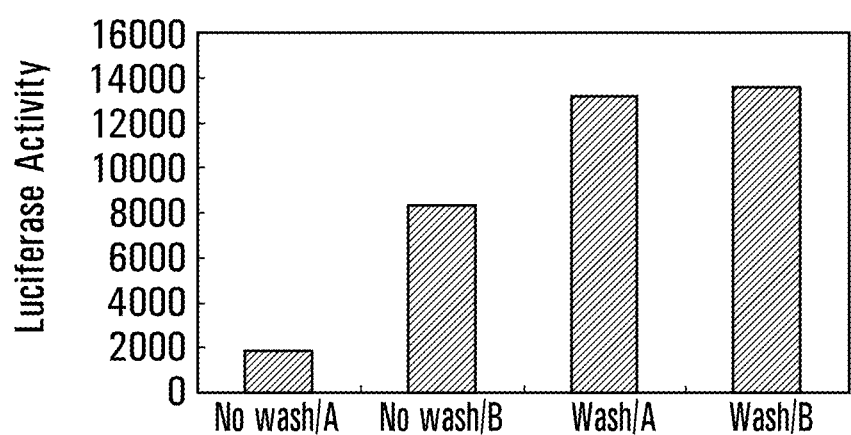
FIG. 13 shows the anti-HIV-1 activities of Formulations A and B.
Figure 14A:
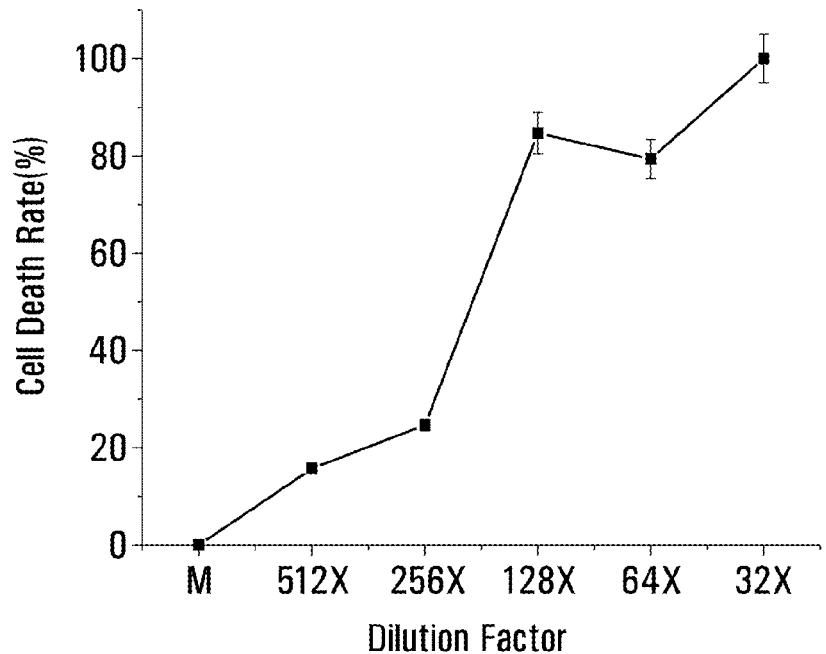
FIGS. 14A to 14D show the cell toxicity effects of Formulations A (FIG. 14A) and B (FIG. 14B) and the HIV-1 inhibitory activities of Formulations A (FIG. 14C) and B (FIG. 14D). The error bars represent standard deviations (±SD).
Figure 14B:
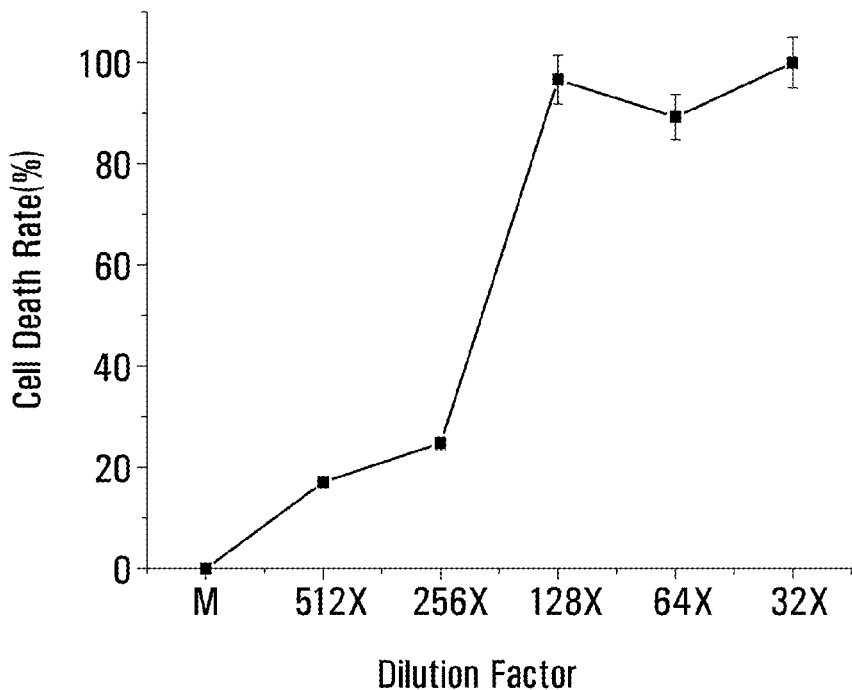
Figure 14C:
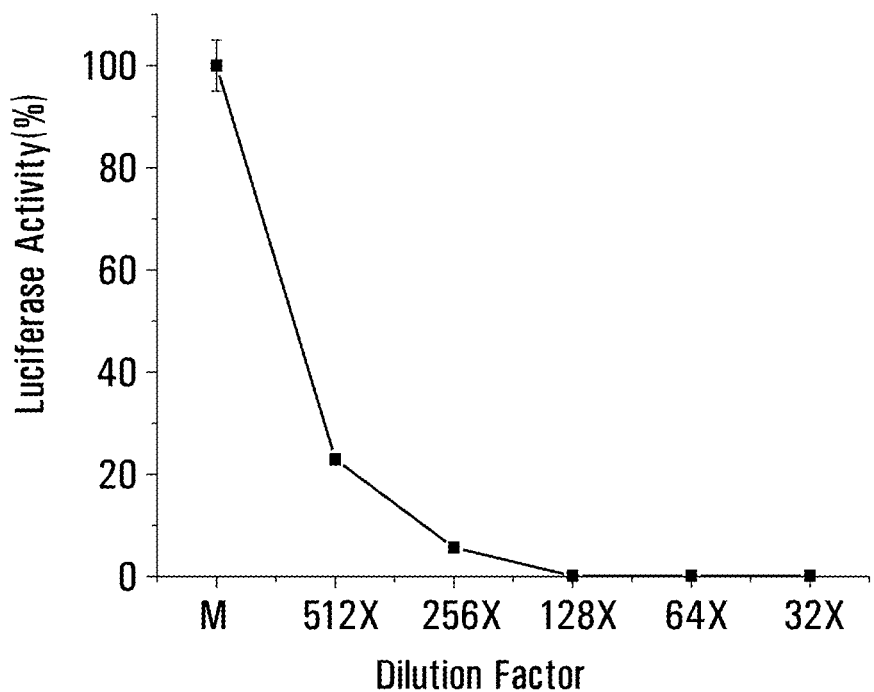
Figure 14D:
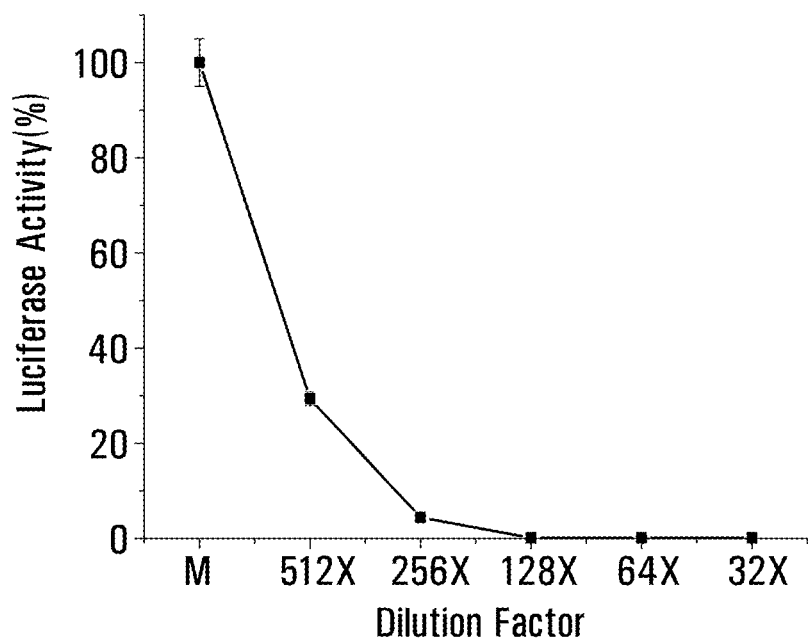

The results of experimental procedures 6A, 6B, 6C, 6D and 6E are shown in FIGS. 9, 10, 11, 12, and 13 respectively. As can be seen in FIG. 9, the HIV-1 inhibitory activities of Formulation A to C lacked dose-dependent relationship. Based on the results shown in FIG. 11, the IC50 of Formulation B was estimated to be at a dilution factor of about 36×. As can be seen in FIG. 12, the presence of human semen did not affect the anti-viral activity of Formulation B. Based on the results shown in FIG. 13, Formulations A and B inhibited HIV-1 infections at a non-toxic concentration (see FIG. 8 which shows that at the dilution factor of 324×, Formulations A and B did not significantly reduce cell viability).

Without being limited by theory, it is believed that the anti-viral activity of Formulation B is unlikely due to its acidic nature since the pH of the diluted solutions (Formulation B diluted in the culture media) was close that of the culture media.

Example 7: Examination of Toxicity and Anti-HIV-1 Activity in One System

Materials

CytoTox-ONE™ Homogeneous Membrane Integrity Assay was purchased from Promega, USA. Formulations A and B identified in Example 1 were tested.

Experimental Procedure

Cytotoxicity was determined by the Homogeneous Membrane Integrity Assay which measures the release of lactate dehydrogenase (LDH) from Ghost R5X4 cells with a damaged membrane. The released LDH results in the conversion of resazurin into resorufin. The generation of the fluorescent resorufin product is proportional to the amount of LDH.

The specific steps are as follows:
1. The cytotoxicity studies were carried out on the target cells to establish cell viability-formulation dosage relationship curves under the conditions identical to those needed for performing LDH release assay, with 37° C. to 22° C. transition, and to accurately determine the transition concentrations (Points A) and CC50% (Point B). The Transition concentration and CC50% were used for the LDH release analyses.
2. Opaque-walled tissue culture plates containing cells in relevant culture medium were set up.
3. The formulations and vehicle controls were added to appropriate wells so the final volume is 100 μL in each well. The amount of the formulation added was determined by the Transition concentrations (Point A) and CC50% (Point B), respectively.
4. The cells were cultured for 2 hrs in a 37° C., 5% CO2 incubator.
5. Assay plates were removed from the 37° C. incubator and equilibrated to 22° C. (approximately 20-30 minutes).
6. A volume of CytoTox-ONE Reagent equal to the volume of cell culture medium present in each well was added and mixed or shaken for 30 seconds (e.g., add 100 μL of CytoTox-ONE Reagent to 100 μL of medium containing cells for the 96-well plate format).
7. The culture plates were incubated at 22° C. for 10 minutes.
8. 50 μL of Stop Solution (per 100 μL of CytoTox-ONE Reagent added) was added to each well. This step is optional but recommended for consistency.
9. The plates were shaken for 10 seconds and fluorescence was recorded with an excitation wavelength of 560 nm and an emission wavelength of 590 nm.

In an identical system, the cells were treated with Formulations A and B and then infected with CNE33 pseudotyped virus stocks and the effect on the viral infectivity was determined by measuring luciferase activity that is controlled by viral LTR.

The specific steps are as follows:
1. In a separate but parallel analysis, the culture plates were set up identically and the cells were treated with or without corresponding dilutions of the formulations under identical conditions.
2. The formulations were either removed by washing with culture medium or remained in the culture. Pseudotyped viruses were added to the culture plates to infect the cells and the infection was measured by luciferase activities.
3. The infections were quantified to determine the differential roles of the formulations on cellular membrane disruption and viral inactivation.
4. The pseudotyped viruses were also treated with corresponding concentrations (Transition concentrations and CC50%) of the formulations under conditions identical to those for the target cells, and the formulations were removed by ultra-centrifugation or size exclusion gel filtration chromatography. Then the viruses were used to infect the target cells and the effect of the formulations on the viral infectivity were quantified.

Each dilution was in triplicate and the experiments were repeated once.

Results

The results of one representative experiment were shown in FIGS. 14A to 14D. Formulations A and B showed similar cytotoxicity profiles with CC50 values at dilution factors of between 128× and 256× (estimated to be about 192×). At higher concentrations (32×~128× dilution), cytotoxicity increased dramatically. At dilution factors of 256× or more, the cytotoxicity was low in comparison with the mock-treated cells.

At the dilution factor of 256×, Formulations A and B showed 94.3% and 95.6% inhibition of HIV-1 infection while the cell viabilities at this concentration were approximately 70%. At the dilution factor of 512×, the viral infection was inhibited by 77.1% and 70.6% for Formulations A and B, respectively, while the cell viabilities at this concentration were higher than 80%.

The inhibition of the viral infection at the dilution factors of 256× and 512× is unlikely caused by the reduction of viable target cells. Without being limited by theory, it is possible that the target cell membrane is less sensitive to the surfactant disruption than the virus.

Example 8: Anti-HSV-2 Activity

Materials

Formulations A and B identified in Example 1 were tested.

Experimental Procedure

The HSV-2 infection and inhibition assays were performed in Hec-1a cells. Therefore, the cytotoxicity of Formulations A and B to Hec-1a cells was analyzed. Hec-1a cells were cultured with M5A medium supplemented with penicillin (100 units/ml), streptomycin (100 ug/ml) and FCS (10%), in the presence of Formulation A or B, respectively. The viability of cells after 24 h culture was determined by using cell counting kit-8 (Dojindo Molecular Technologies, Inc, US) following the manufacturer's protocols. OD405 was measured by a Tecan T200 system. The cytotoxicity of the gel was expressed by Membrane Damage Index (MDI), which was calculated as MDI (%)=(OD405 of Sample−OD450 of Mock)/OD450 of Mock. Average and standard deviation were calculated from triplicate determinations.

Two assays were utilized for the determination of the inhibitory activity of Formulations A and B on HSV-2 infection.

The first assay was In-Cell Western assay. HSV-2 stocks were incubated with Formulation A or B in a series of dilutions for 30 min in room temperature. Hec-1-a cells were infected with the HSV-2 stock post drug treatment. After 24 h culture, the cells were harvested and analyzed by an In-Cell Western assay for the determination of gD expression. Average and standard deviation were calculated from the triplicate wells. HSV-2 replication levels were indicated by gD expression levels. The inhibitory assay was performed twice independently.

The second assay was Recombinant HSV-2 Expressing Luciferase assay. Recombinant HSV-2 expressing luciferase (Luci-HSV-2) stocks were incubated with Formulation A or B in a series of dilutions for 30 min in room temperature. Vero-ICP10 cells were infected with the Luci-HSV-2 post drug treatment. The cells cultured in the absence of virus and cells infected with the Luci-HSV-2 naive to drug treatment were included as cell control and virus control, respectively. After 24 h culture, the cells were harvested and determined for luciferase activity (LA value). The inhibition rate was calculated as inhibition rate=1−[(LAsample-LACell control)/(LAVirus control-LAcell control)].

Results

Figure 15A:
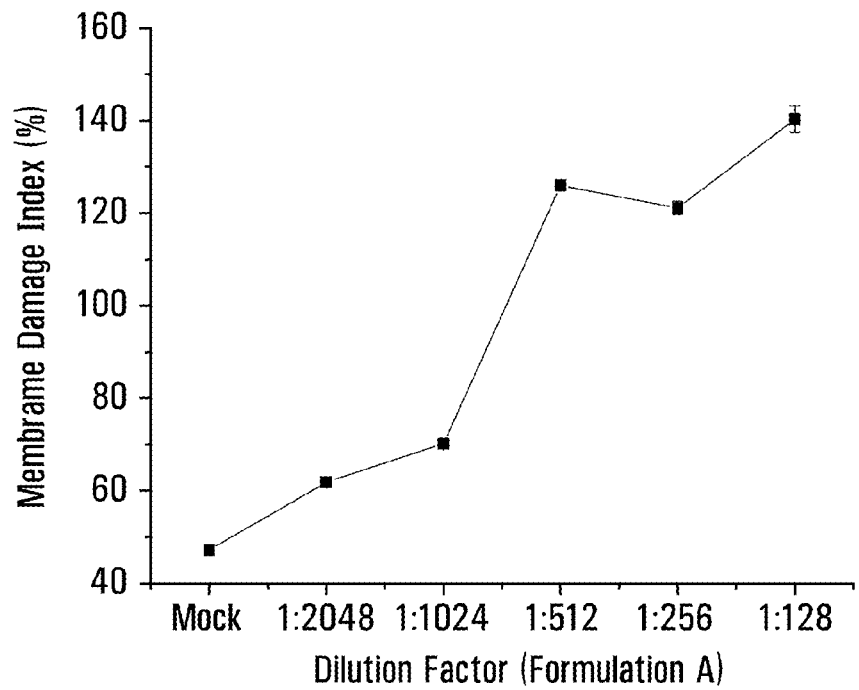
FIGS. 15A to 15F show the cell toxicity effects of Formulations A (FIG. 15A) and B (FIG. 15B) and the HSV-2 inhibitory activities of Formulations A (FIG. 15C and FIG. 15E) and B (FIG. 15D and FIG. 15F). The error bars represent standard deviations (±SD).
Figure 15B:
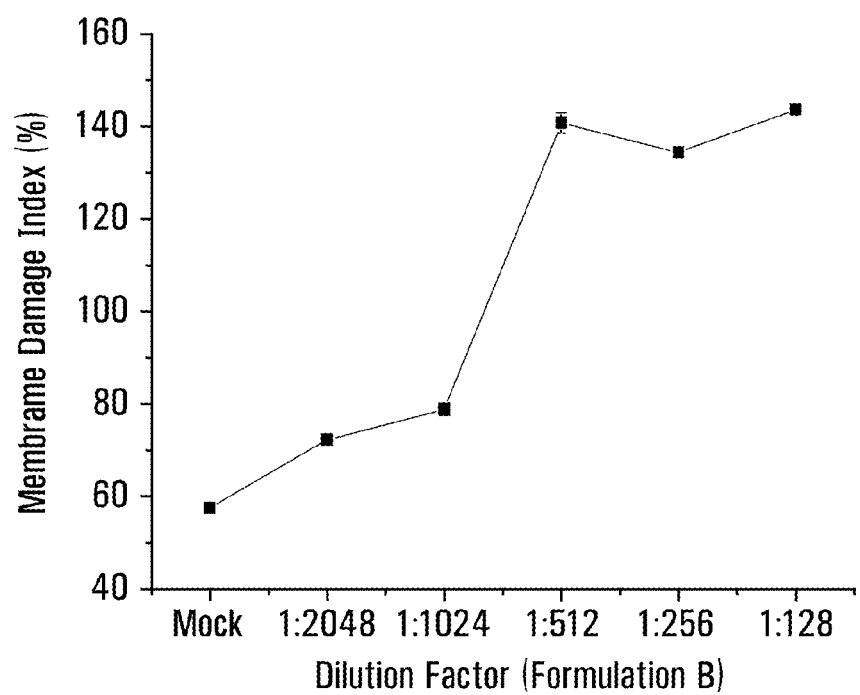
Figure 15C:
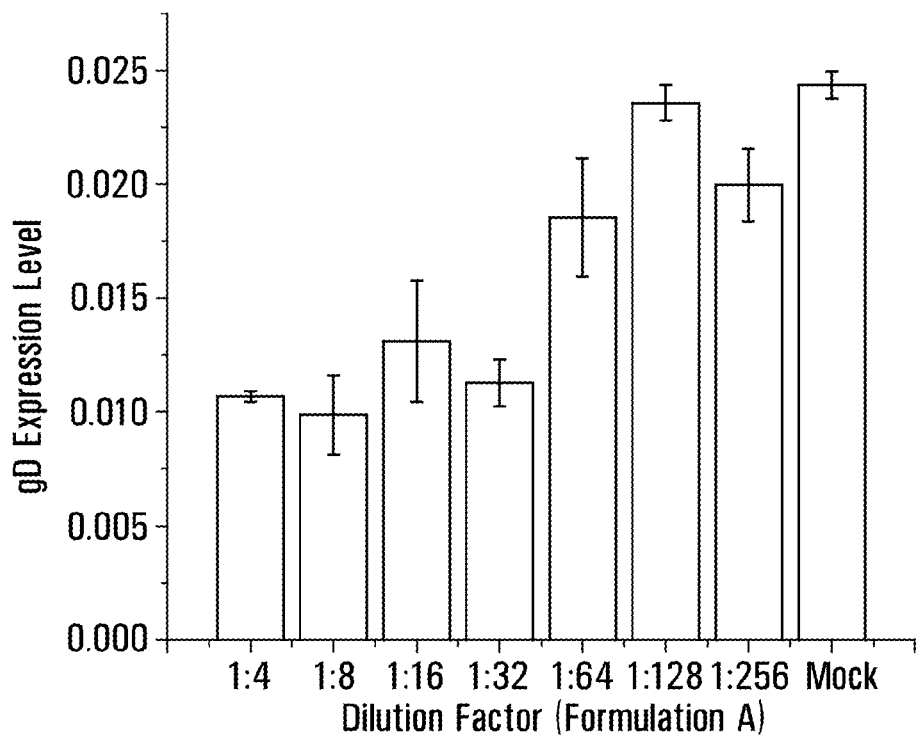
Figure 15D:
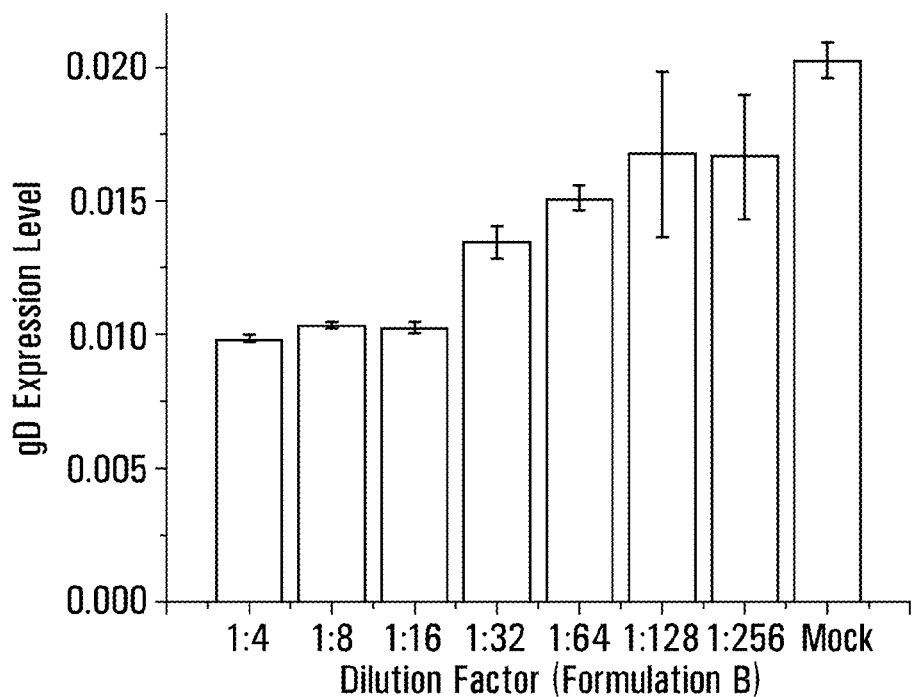
Figure 15E:
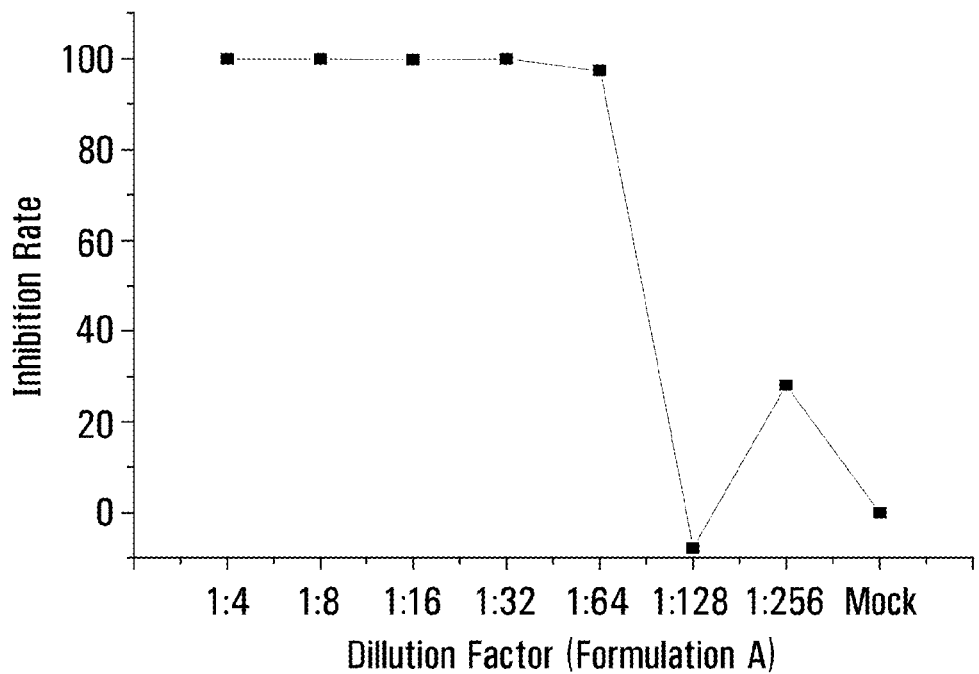
Figure 15F:
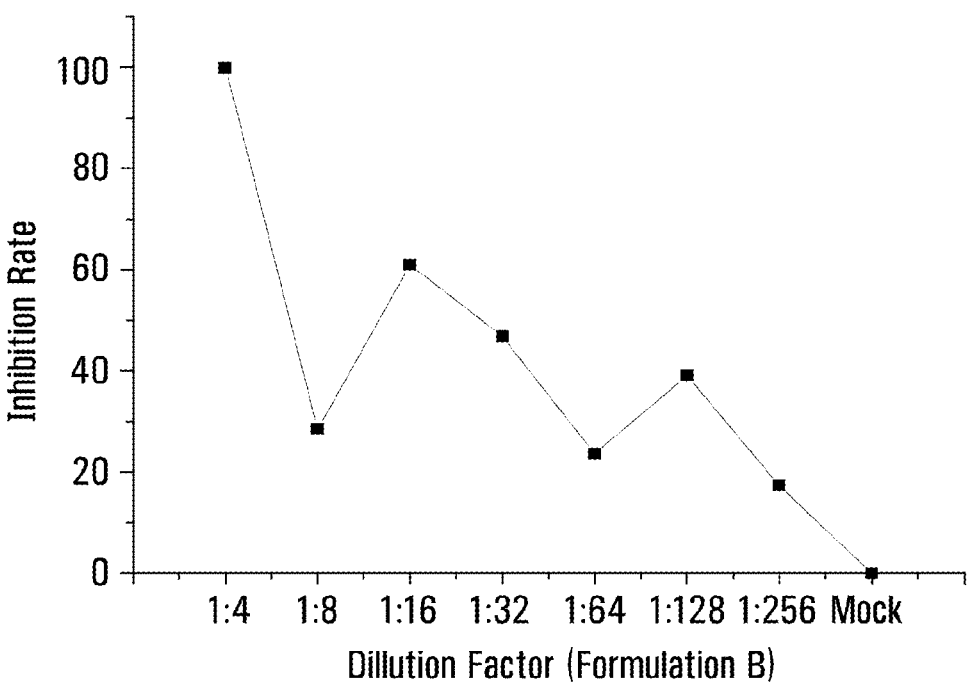

The cytotoxicity results were shown in FIGS. 15A and 15B. The In-Cell Western assay results were shown in FIGS. 15C and 15D. The Recombinant HSV-2 Expressing Luciferase assay results were shown in FIGS. 15E and 15F. Formulation A achieved an inhibition rate of 97.3% at a dilution of 1:64, and an inhibition rate of 99.8% at a dilution of 1:32. Formulation B achieved an inhibition rate of 99.8% at a dilution of 1:4.

Example 9: Clearance of Viruses

Materials

HIV strain HTLV-IIIb supplied by National Cancer Institute, Bethesda, Md., USA and PSR strain Bartha K61 (Duphar, Weesp, the Netherlands 1991) were used.

Experimental Procedure

The experiments were performed following Virus Safety Services, Final Report 5002, Testing of virus inactivating capacity of "Liquid Gel", Sanquin Blood Supply, Plesmanlaan 125, 1066 CX Amsterdam, the Netherlands.

Results

As shown in Table 2, complete clearance was found in resulting >4.8 log 10 for HIV and 5.0 log 10 for PSR after 20 seconds of treatment (experimental setting including 20 sec mixing).

TABLE 2

| | Clearance of Viruses (CF (log10) ± 95% CL): | | | | |
|---|---|---|---|---|---|
| Virus | exp | 20 sec. | 40 sec. | 1 min. | 5 min. |
| HIV | 231 | >4.8 ± 0.2 | >4.8 ± 0.2 | >4.8 ± 0.2 | >4.8 ± 0.2 |
| PSR | 200 | >5.0 ± 0.2 | >5.0 ± 0.2 | >5.0 ± 0.2 | >5.0 ± 0.2 |

Example 10: Spermicidal Activity

Materials

Formulation B identified in Example 1 was tested.

Experimental Procedure

1. Formulation B was mixed with fresh semen at ratios of 4:1, 1:1 and 1:4 in a total volume of 1 mL, and the mixture was incubated at 37° C. for 10-30 min. Saline was used as a control.
2. The sperms were stained and live sperms and total sperms were counted under light microscope.
3. The pH of the mixture was determined.
4. Optionally, another mixture was incubated for 30 min and the sperms were examined on a hemocytometer under light microscope. The swollenness of the sperms were determined by measuring the diameters of the neck region of the sperms.
5. Sperm analyzer was used to analyze the sperm parameters and the sperm mobility was graded in four levels: A level—fast forward; B level—slow forward; C level—swing in place and D level—no motion. The number of sperms were counted at different levels and maps of trajectory were constructed.
6. The mixture was further incubated for 30 min and the viscosity was measured.

Results

Figure 16:
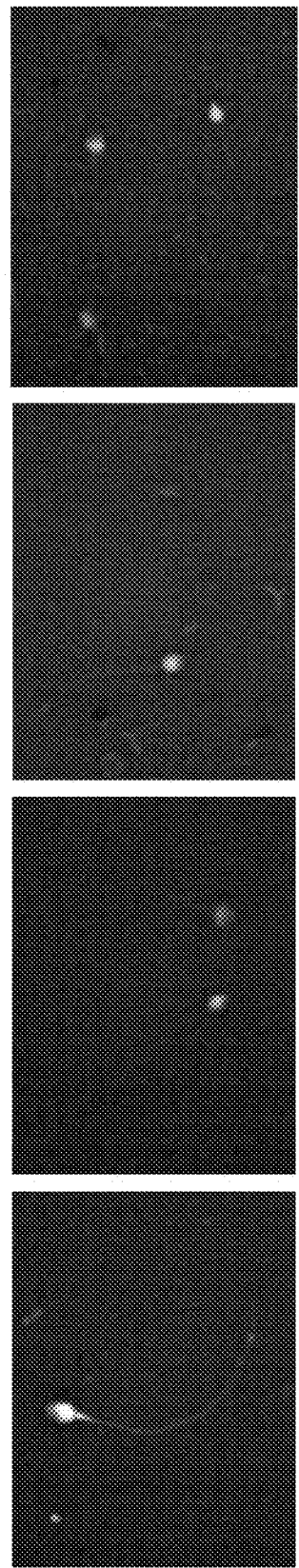
FIG. 16 are representative microscopic pictures of sperm treated with or without Formulation B.

The results were shown in Table 3 and FIG. 16.

TABLE 3

| | Semen pH | Sperm conc. (No/mL) | Sperm motility (%) | Forward movement (%) |
|---|---|---|---|---|
| Control | 7.4 | 102.54 ± 5.12 | 33.76 ± 3.75 | 25.46 ± 3.0 |
| Semen:Formulation B = 4:1 | 7.4 | 72.23 ± 4.35 | 0 | 0 |
| Semen:Formulation B = 1:1 | 7.4 | 49.25 ± 3.28 | 0 | 0 |
| Semen:Formulation B = 1:4 | 7.4 | 24.33 ± 2.85 | 0 | 0 |

Example 11: Anti-Viral Activity in Comparison with Dextran Sulfate (DXS) and Azidothymidine (AZT)

Materials

Formulation B identified in Example 1 was tested. DXS and AZT were purchased from Sigma-Aldrich.

Experimental Procedure

1. Ghost R5X4 cells were seeded into 96-well plate at a density of $2 \times 10^4$ per well.
2. After cells reached confluence, 50 μl 4000TCID50/ml HIV-1 (strain SF162) pseudotyped virus were added.
3. At indicated time points, AZT (1 μg/mL), DXS (100 μg/mL) or Formulation B (240× dilution) was added.
4. The cells were cultured for 48 hrs, and the luciferase activity was measured.

Results

Figure 17:
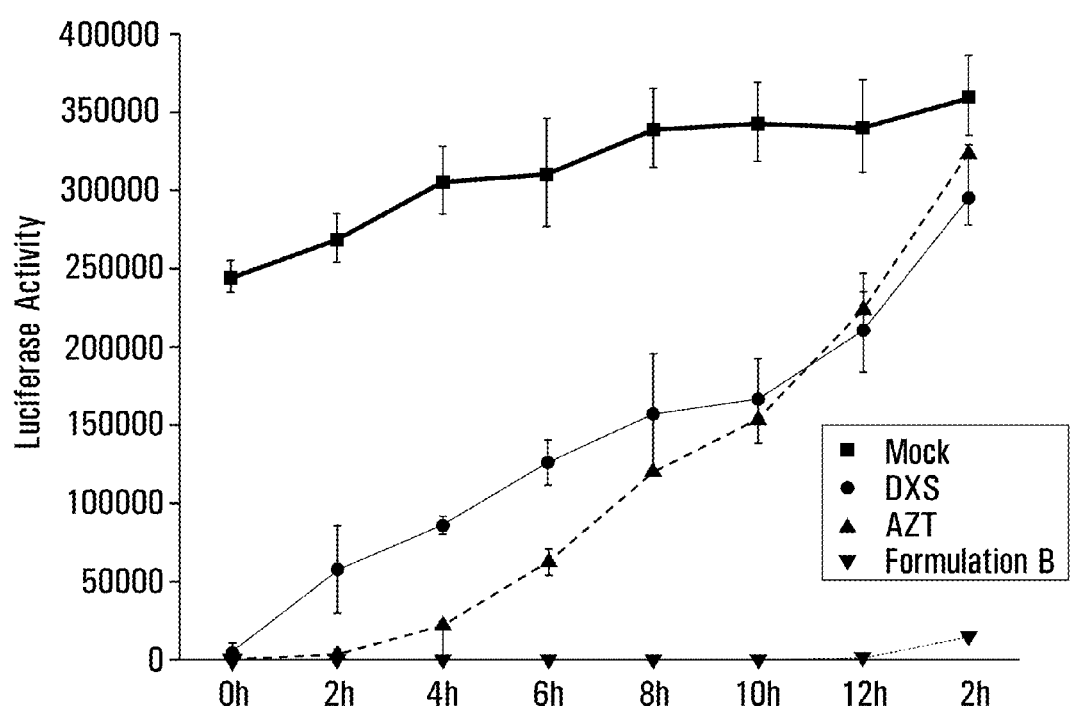
FIG. 17 shows anti-HIV activities of Formulation B, dextran sulfate and azidothymidine.

As shown in FIG. 17, Formulation B inactivated the virus instantaneously and during the entire time span of the viral replication cycle.

Example 12: Inhibitory Activity Against *Gonococci* and *Chlamydia trachomatis*

The inhibitory activity of the formulations of the present invention against *gonococci* is determined by Kirby-Bauer testing and a standard Minimum Inhibitory Concentration (MIC) assay.

The inhibitory activity of the formulations of the present invention against *Chlamydia trachomatis* is determined by testing the growth decline of *Chlamydia trachomatis* in susceptible cells (such as Hela 229 cells).

Example 13: Cytotoxicity and Anti-HIV-1 Activity on TZM-b1 Cells

Materials

TZM-b1 cells were provided by NIH AIDS Research & Reference Reagent Program and Vero cells by American Type Culture Collection (ATCC, Rockville, Md.). HIV-$1_{ADA-M}$ and HIV-$1_{MN}$ were provided by Dr. Jeff Lifson at Leidos Biomedical Research, Inc., Frederick National Laboratory. TZM-b1 and Vero cells are stored at −150° C. HIV-$1_{ADA-M}$ and HIV-$1_{MN}$ strains are stored at −80° C.

Experimental Procedure

Cytotoxicity and anti-HIV activity were tested using TZM-b1 cells. Briefly, TZM-b1 cells were plated ($1.5 \times 10^4$ cells/well) in 100 μL of propagation medium and incubated overnight at 37° C., 5% $CO_2$, and 98% humidity (standard conditions). Matrine, IGEPAL®CA-6300 and Matrine:IGEPAL®CA-630 (4:1 combination) were diluted in propagation medium to obtain 2× dilutions of the appropriate dilution range (a total of eight different dilutions per sample). Matrine raised the pH of propagation medium to close to 10, and the pH had to be adjusted to 7.5 using 1N HCl before preparing Matrine dilutions and adding to cells. IGEPAL®CA-630 in propagation medium showed a pH of 7.5 and there was no need to adjust pH. Cell culture media on the cell monolayers was replaced with 50 μl of the diluted compounds or 50-100 μL of medium for virus and cell controls. Dilutions were tested in triplicate. 50 μL of HIV-$1_{ADA-M}$ and HIV-$1_{MN}$ (about 100 infectious units per well) were added immediately after compounds to all wells (with the exception of cell controls) and incubated for 72 h at standard conditions ('No wash'). Alternatively, the cell monolayers were washed four hours after virus challenge and fresh propagation medium was added before incubation for 72 h at standard conditions ('Wash'). The final range of compound concentrations tested in the cytotoxicity and antiviral assays are shown in Table 4. The percentage of virus replication was estimated using the multinuclear activation of a galactosidase indicator (MAGI) assay. Cytotoxicity (looking at percentage of cell viability) was estimated using the XTT or CyQuant assays, mimicking the antiviral assay but without virus. MIV-150 and Tween-20 were used as internal controls for antiviral activity (TZM-b1 assay) and cytotoxicity (XTT and CyQuant assays) respectively.

Results

The cytotoxicity (measured as $CC_{50}$% (w/v)) results were shown in Table 5. The antiviral activity (measured as $EC_{50}$% (w/v)) results were shown in Table 6. The values of therapeutic index ('TI') which is the ratio of $CC_{50}$ over $EC_{50}$ for each combination of cytotoxicity assay and HIV strain were shown in Table 7. Notably, for each combination, the TI value of the Matrine:IGEPAL®CA-630 combination is higher than that of IGEPAL®CA-630 alone.

TABLE 4

| Compound | Percentage of compound (w/v) |
| --- | --- |
| Matrine | 1.0000; 0.3333; 0.1111; 0.0370; 0.0123; 0.0041; 0.0014; 0.0005 |
| IGEPAL | 0.2500; 0.0833; 0.0278; 0.0093; 0.0031; 0.0010; 0.0003; 0.0001 |
| Matrine:IGEPAL (4:1) | 1.0000:1.2500; 0.3333:0.0833; 0.1111:0.0278; 0.0370:0.0093; 0.0123:0.0031; 0.0041:0.0370; 0.0014:0.0003; 0.0005:0.0001 |

TABLE 5

| | $CC_{50}$ % (w/v) | | | |
| --- | --- | --- | --- | --- |
| | CyQuant | | XTT | |
| Compound | Wash | No wash | Wash | No wash |
| Matrine | 0.3530 | 0.6240 | 1.1040 | 0.3122 |
| IGEPAL | 0.0048 | 0.0036 | 0.0072 | 0.0002 |
| Matrine:IGEPAL (4:1) | 0.0085 | 0.0049 | 0.0083 | 0.0002 |

TABLE 6

| | $EC_{50}$ % (w/v) | | | |
| --- | --- | --- | --- | --- |
| | HIV-1MN | | HIV-1ADA-M | |
| Compound | Wash | No wash | Wash | No wash |
| Matrine | 0.0500 | 0.0700 | 0.3948 | 0.2075 |
| IGEPAL | 0.0031 | 0.0012 | 0.0035 | 0.00037 |
| Matrine:IGEPAL (4:1) | 0.0030 | 0.0007 | 0.0034 | 0.0001 |

TABLE 7

| | TI ($CC_{50}/EC_{50}$) | | | | | | | |
| --- | --- | --- | --- | --- | --- | --- | --- | --- |
| | CyQuant/ HIV-1MN | | CyQuant/ HIV-1ADA-M | | XTT/ HIV-1MN | | XTT/HIV-1ADA-M | |
| Compound | Wash | No wash | Wash | No wash | Wash | No wash | Wash | No wash |
| Matrine | 7.06 | 8.91 | 0.89 | 3.01 | 22.08 | 4.46 | 2.80 | 1.50 |
| IGEPAL | 1.55 | 2.95 | 1.38 | 9.73 | 2.31 | 0.13 | 2.05 | 0.43 |
| Matrine:IGEPAL (4:1) | 2.84 | 7.00 | 2.48 | 49.00 | 2.76 | 0.29 | 2.41 | 2.00 |

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the scope of the appended claims.

It must be noted that as used in this specification and the appended claims, the singular forms "a," "an," and "the" include plural reference unless the context clearly dictates otherwise. Unless defined otherwise all technical and scientific terms used herein have the same meaning as commonly understood to one of ordinary skill in the art to which this invention belongs.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to encompass the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items:

As used herein, whether in the specification or the appended claims, the transitional terms "comprising", "including", "carrying", "having", "containing", "involving", and the like are to be understood as being inclusive or open-ended (i.e., to mean including but not limited to), and they do not exclude unrecited elements, materials or method steps. Only the transitional phrases "consisting of" and "consisting essentially of", respectively, are closed or semi-closed transitional phrases with respect to claims and exemplary embodiment paragraphs herein. The transitional phrase "consisting of" excludes any element, step, or ingredient which is not specifically recited. The transitional phrase "consisting essentially of" limits the scope to the specified elements, materials or steps and to those that do not materially affect the basic characteristic(s) of the invention disclosed and/or claimed herein.

The invention claimed is:

1. A method of increasing the therapeutic index of an octoxynol, said method comprising administering (a) a quinolizidine alkaloid compound; and (b) the octoxynol to a mucosal membrane of a subject, wherein the quinolizidine alkaloid compound increases the therapeutic index of the octoxynol to said mucosal membrane, and wherein the quinolizidine alkaloid compound has a structure:

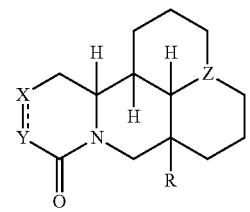

or a pharmaceutically acceptable salt, solvate or stereoisomer thereof, wherein:
R is H or OH;
X and Y are each $CH_2$ or CH; and
Z is N or NO.

2. The method of claim 1, wherein the composition is formulated as a gel, and wherein when the subject is a human female, the administration comprises discharging the composition into the vagina or anus of the human female, and when the subject is a human male, the administration comprises discharging the composition into the anus of the human male.

3. The method of claim 1, wherein the quinolizidine alkaloid compound is matrine and/or oxymatrine.

4. The method of claim 1, wherein the octoxynol is octoxynol-9.

5. The method of claim 3, wherein the composition comprises about 0.4% of matrine and/or oxymatrine on a weight (g)/volume (mL) basis.

6. The method of claim 4, wherein the composition comprises about 0.1% of octoxynol-9 on a volume/volume (mL) basis.

7. The method of claim 2, wherein the method reduces the incidence of conception.

8. The method of claim 2, wherein the method results in reduced transmission of a sexually transmitted disease infection.

9. The method of claim 8, wherein the sexually transmitted disease is caused by infection of human immunodeficiency virus (HIV) or herpes simplex virus 2 (HSV-2).

* * * * *